(12) United States Patent
Plum et al.

(10) Patent No.: US 8,937,042 B2
(45) Date of Patent: Jan. 20, 2015

(54) PHARMACEUTICAL COMPOSITIONS COMPRISING GLP-1 PEPTIDES OR EXTENDIN-4 AND A BASAL INSULIN PEPTIDE

(75) Inventors: Anne Plum, Birkerød (DK); Dorte Bjerre Steensgaard, Copenhagen (DK); Jens Kaalby Thomsen, Hellerup (DK); Morten Schlein, Lyngby (DK); Anne Sofie Kajær Markussen, Værløse (DK); Christian Poulsen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 140 days.

(21) Appl. No.: 12/741,923

(22) PCT Filed: Nov. 14, 2008

(86) PCT No.: PCT/EP2008/065601
§ 371 (c)(1),
(2), (4) Date: Aug. 5, 2010

(87) PCT Pub. No.: WO2009/063072
PCT Pub. Date: May 22, 2009

(65) Prior Publication Data
US 2011/0152185 A1   Jun. 23, 2011

Related U.S. Application Data

(60) Provisional application No. 60/989,462, filed on Nov. 21, 2007.

(30) Foreign Application Priority Data

Nov. 16, 2007 (EP) .................................. 07120880

(51) Int. Cl.
| | | |
|---|---|---|
| *A61K 38/28* | (2006.01) | |
| *A61K 38/26* | (2006.01) | |
| *C07K 14/605* | (2006.01) | |
| *C07K 14/62* | (2006.01) | |
| *A61K 38/00* | (2006.01) | |

(52) U.S. Cl.
CPC ............... *C07K 14/605* (2013.01); *C07K 14/62* (2013.01); *A61K 38/00* (2013.01)
USPC ................. 514/6.5; 514/6.4; 514/7.2

(58) Field of Classification Search
None
See application file for complete search history.

(56) References Cited

U.S. PATENT DOCUMENTS

| | | | |
|---|---|---|---|
| 6,686,177 B1 * | 2/2004 | Ertl et al. ...................... | 435/69.4 |
| 6,989,148 B2 | 1/2006 | Dupre | |
| 7,179,788 B2 | 2/2007 | DeFelippis et al. | |
| 7,238,663 B2 | 7/2007 | DeFelippis et al. | |
| 2001/0041786 A1 | 11/2001 | Brader et al. | |
| 2005/0203002 A1 * | 9/2005 | Tzannis et al. ................... | 514/4 |
| 2006/0247167 A1 * | 11/2006 | Schlein et al. .................. | 514/12 |
| 2006/0287221 A1 * | 12/2006 | Knudsen et al. ................... | 514/3 |
| 2009/0011976 A1 * | 1/2009 | Ludvigsen et al. ............... | 514/4 |

FOREIGN PATENT DOCUMENTS

| | | |
|---|---|---|
| CN | 1635900 A | 7/2005 |
| GB | 2114573 | 8/1983 |
| JP | 2002532557 A | 10/2002 |
| JP | 2003-503356 A | 1/2003 |
| JP | 2003-505347 | 2/2003 |
| WO | WO 95/31214 | 11/1995 |
| WO | WO 98/08871 | 3/1998 |
| WO | 99/32116 A1 | 7/1999 |
| WO | WO 99/43706 | 9/1999 |
| WO | WO 00/37098 | 6/2000 |
| WO | WO 01/00223 | 1/2001 |
| WO | WO 02/00223 | 1/2002 |
| WO | WO 03/020201 | 3/2003 |
| WO | 03/094956 A1 | 11/2003 |
| WO | WO 2005/046716 | 5/2005 |
| WO | 2006/014673 A2 | 2/2006 |
| WO | WO 2006/029634 | 3/2006 |
| WO | WO 2006/051103 | 5/2006 |
| WO | WO 2007/074133 | 7/2007 |
| WO | 2007/128817 A2 | 11/2007 |

OTHER PUBLICATIONS

Non-Final Office Action mailed Dec. 8, 2010 for U.S. Appl. No. 11/667,037, filed May 3, 2007 by Ludvigsen et al.
Larsen, et al Diabetes Systemic Administration of the Long-Acting GLP-1 Derivative NN2211 Induces Lasting and Reversible Weight Loss in Both Normal and Obese Rats 2001 50-2530-2539.
European Medicines Agency, Evaluation of Medicines for Human Use, Assessment Report for Victoza®, 2009, Doc. Ref.: EMEA/379172/2009.
Levemir® Product Insert from Novo Nordisk, Jun. 16, 2005.

* cited by examiner

*Primary Examiner* — Gyan Chandra
(74) *Attorney, Agent, or Firm* — Rosemarie R. Wilk-Orescan

(57) ABSTRACT

Pharmaceutical composition for parenteral administration comprising a basal insulin peptide and an insulinotropic GLP-1 peptide comprising at least 6 zinc atoms per 6 insulin molecules.

3 Claims, 8 Drawing Sheets

PHARMACEUTICAL COMPOSITIONS COMPRISING GLP-1 PEPTIDES OR EXTENDIN-4 AND A BASAL INSULIN PEPTIDE

CROSS-REFERENCE TO RELATED APPLICATIONS

This application is a 35 U.S.C. §371 national stage application of International Patent Application PCT/EP2008/065601 (published as WO 2009/063072), filed Nov. 14, 2008, which claimed priority of European Patent Application 07120880.5, filed Nov. 16, 2007; this application further claims priority under 35 U.S.C. §119 of U.S. Provisional Application 60/989,462, filed Nov. 21, 2007.

FIELD OF THE INVENTION

The present invention relates to the field of pharmaceutical compositions. More specifically the invention relates to pharmaceutical compositions comprising two different pharmaceutically active peptides.

BACKGROUND OF THE INVENTION

Diabetes mellitus is a metabolic disorder in which the ability to utilize glucose is partly or completely lost. Since the introduction of insulin in the 1920's, continuous efforts have been made to improve the treatment of diabetes mellitus. Since people suffering from diabetes are subject to chronic treatment over several decades, there is a major need for safe, convenient and life quality improving insulin formulations.

In the treatment of diabetes mellitus, many varieties of insulin formulations have been suggested and used, such as regular insulin, isophane insulin (designated NPH), insulin zinc suspensions (such as Semilente®, Lente®, and Ultralent®), and biphasic isophane insulin. Some of the commercial available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both. Within the last decade a number of human insulin analogues have been developed. They are designed for particular profiles of action, i.e. fast acting or prolonged action.

Another peptide expected to become very important in the treatment of diabetes is glucagon-like peptide-1 (GLP-1). Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. GLP-1 stimulates insulin secretion in a glucose-dependant manner, stimulates insulin biosynthesis, promotes beta cell rescue, decreases glucagon secretion, gastric emptying and food intake. As the type 2 diabetes population is rapidly increasing in the world there is a much larger need for simpler administration of more effective drugs. A combination formulation comprising an insulin peptide and a GLP-1 peptide with a fixed ratio of the two pharmaceuticals may be a very efficacious treatment as well as one requiring less injections when administered to the same patient.

A combined treatment of insulin requiring diabetes comprising administration of insulin and GLP-1 is disclosed in WO 95/31214. Pre-mixed formulation of GLP-1 compounds and basal insulin are disclosed in WO 03/020201. Shelf stable pharmaceutical compositions comprising GLP-1, a basal insulin and surfactants are disclosed in WO 2006/051103.

SUMMARY OF THE INVENTION

Figure 1:
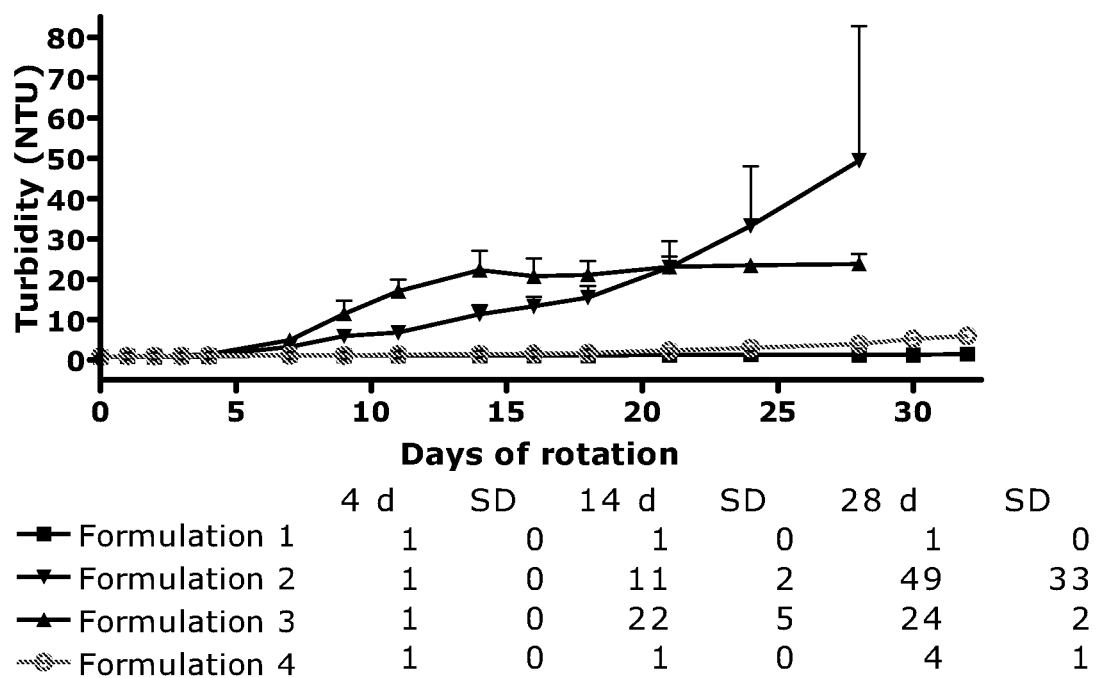
FIG. 1 shows the physical stability of four pharmaceutical compositions evaluated by means of an accelerated stressed test.

One object of the present invention is to provide a shelf-stable once daily fixed combination of a GLP-1 compound and a basal insulin compound with unchanged PK/PD properties of the combined peptides compared to the individual active components.

More specifically the invention is related to a shelf-stable pharmaceutical composition comprising a fixed combination of an insulinotropic GLP-1 compound and a basal insulin which composition contains at least 5 zinc ions per 6 basal insulin molecules.

In one embodiment the pharmaceutical composition contains at least 6 zinc ions per 6 basal insulin molecules.

In another embodiment the pharmaceutical composition contains at least 7 zinc ions per 6 basal insulin molecules.

In another embodiment the pharmaceutical composition contains at least 8 zinc ions per 6 basal insulin molecules.

In a further embodiment the pharmaceutical composition contains at least 9; 10; 11; 12; 13; 14; 15; or 16 zinc ions per 6 basal insulin molecules.

In one embodiment the zinc content is between 5 and 16 zinc ions per 6 insulin molecules.

In a another embodiment the zinc content is between 5 and 15; 5 and 14; 5 and 13; 5 and 12; 5 and 11; 5 and 10; 5 and 9, 5 and 8 or between 5 and 7 zinc ions per 6 insulin molecules.

In a further embodiment the zinc content is between 6 and 16 zinc ions per 6 insulin molecules.

In a further embodiment the zinc content is between 6 and 15; 6 and 14; 6 and 13; 6 and 12; 6 and 11; 6 and 10; 6 and 9 or between 6 and 8 zinc ions per 6 insulin molecules.

In another embodiment the zinc content is between 7 and 16 zinc ions per 6 insulin molecules.

In a further embodiment the zinc content is between 7 and 14; 7 and 15; 7 and 14; 7 and 13; 7 and 12; 7 and 11; 7 to 10; or 7 and 9 zinc ions per 6 basal insulin molecules.

In another embodiment the zinc content is between 8 and 16 zinc ions per 6 insulin molecules.

In another embodiment the zinc content is between 8 and 15; 8 and 14; 8 and 13; 8 and 12; 8 and 11; or 8 and 10 zinc ions per 6 insulin molecules.

The pH of the pharmaceutical formulation will in any of the above embodiments typically be above neutral and will typically be between about 7 and about 9.

In one embodiment the pH of the pharmaceutical composition is between about pH 7.4 and about pH 9; between about pH 7.4 and about pH 8.5 or between about pH 7.4 and about pH 8.2.

In another embodiment the pH of the pharmaceutical composition is between about pH 7.5 and about pH 8.5; between about pH 7.5 and about pH 8.2 or between about 7.5 and about 7.7.

In another embodiment the pH of the pharmaceutical composition is from about pH 7.6 to about pH 8.2. In a further embodiment the pH is between about 7.7 and about 8.2.

In another embodiment the pH will be between about 7.7 and about 9.

In another embodiment the pH will be between about 7.7 and about 8.9.

In another embodiment the pH will be between about 7.7 and about 8.8.

In another embodiment the pH will be between about 7.7 and about 8.7.

In another embodiment the pH will be between about 7.7 and about 8.6.

In another embodiment the pH will be between about 7.7 and about 8.5.

In another embodiment the pH will be between about 7.7 and about 8.4.

In another embodiment the pH will be between about 7.7 and about 8.3.

In another embodiment the pH will be between about 7.7 and about 8.2.

In another embodiment the pH will be between about 7.7 and about 8.1.

In another embodiment the pH will be between about 7.7 and about 8.

The insulinotropic GLP-1 compound may in any of the above embodiments be any GLP-1 compound being effective for type 2 treatment. The term "GLP-1 peptide" as used herein means GLP-1(7-37), a GLP-1(7-37) analogue, a GLP-1(7-37) derivative or a derivative of a GLP-1(7-37) analogue. Derivatives of GLP-1 may be acylated GLP1-compounds such as disclosed in WO 98/08871 or WO 2006/097537.

In one embodiment the GLP-1 compound is an acylated GLP-1 analogue such as $Arg^{34}$, $Lys^{26}(N^{\epsilon}$-($\gamma$-Glu($N^{\alpha}$-hexadecanoyl)))-GLP-1(7-37), Aib8,Lys26(OEG-OEG-gamma-Glu-C18-diacid),Arg34)GLP-1 H(7-37)-OH or (N-epsilon26-[2-(2-{2-[2-(2-{2-[(S)-4-Carboxy-4-(17-carboxy-heptadecanoylamino)butyrylamino]ethoxy}ethoxy)acetylamino]ethoxy}ethoxy)-acetyl][Aib8,Arg34]GLP-1-(7-37).

In another embodiment the GLP-1 is exendin-3, exendin-4 or an exendin-4 analogue. The exendin-4-analogue may comprise from 4-10, 4-8 or 4-6 basic amino acid residues added to either the C-terminal or the N-terminal end.

The basal insulin may in any of the above embodiments be any basal insulin known for treatment of type 1 and type 2 diabetes. In one embodiment the basal insulin is an insulin acylated in $\epsilon$-amino group in the B29Lys in the B-chain of insulin and analogues thereof as disclosed in WO 95/07931, WO 2005/012347 and in EP2007/054444.

In another embodiment the basal insulin is a pI shifted basal insulin such as the type disclosed in U.S. Pat. No. 5,656,722 with basic amino acid residue substitutions or additions of the insulin molecule. One example of such basal insulins is GlyA21, ArgB31, ArgB32 human insulin (insulin glargine). Another basal insulin may be an amidated insulin glargine such as the compounds disclosed in WO2008/006496 and WO2008/006497.

In one embodiment the basal insulin is $N^{\epsilon B29}$-tetradecanoyl des(B30) human insulin.

In a further embodiment the basal insulin is $Lys^{B29}(N^{\epsilon}$ lithocholyl-$\gamma$-Glu)-des(B30) human insulin.

In a further embodiment the basal insulin is $N^{\epsilon B29}$-tetradecanoyl des(B30) human insulin or $N^{\epsilon B29}$—($N^{\alpha}$—(HOOC(CH$_2$)$_{14}$CO)-$\gamma$-Glu) desB30 human insulin.

In a further embodiment the basal insulin is $N^{\epsilon B29}$-$\omega$-carboxypentadecanoyl-$\gamma$-L-glutaylamide desB30 human insulin or $N^{\epsilon B29}$-$\omega$-carboxypentadecanoyl-$\gamma$-amino-butanoyl des(B30) human insulin.

In one embodiment the pharmaceutical composition comprises a fixed combination of an insulinotropic GLP-1 compound and an acylated basal insulin selected from the group consisting of $N^{\epsilon B29}$-tetradecanoyl des(B30) human insulin, $Lys^{B29}(N^{\epsilon}$ lithocholyl-$\gamma$-Glu)-des(B30) human insulin, $N^{\epsilon B29}$—($N^{\alpha}$—(HOOC(CH$_2$)$_{14}$CO)-$\gamma$-Glu) desB30 human insulin, $N^{\epsilon B29}$-$\omega$-carboxypentadecanoyl-$\gamma$-L-glutaylamide desB30 human insulin and $N^{\epsilon B29}$-$\omega$-carboxypentadecanoyl-$\gamma$-amino-butanoyl des(B30) human insulin together with suitable pharmaceutically acceptable adjuvants which composition contains at least 5; 6; 7; 8 or 9 zinc atoms per 6 insulin molecules.

In a further embodiment the pharmaceutical composition comprises a fixed combination of an insulinotropic GLP-1 compound and an acylated basal insulin selected from the group consisting of $N^{\epsilon B29}$-tetradecanoyl des(B30) human insulin, $Lys^{B29}(N^{\epsilon}$ lithocholyl-$\gamma$-Glu)-des(B30) human insulin, $N^{\epsilon B29}$—($N^{\alpha}$—(HOOC(CH$_2$)$_{14}$CO)-$\gamma$-Glu) desB30 human insulin, $N^{\epsilon B29}$-$\omega$-carboxypentadecanoyl-$\gamma$-L-glutaylamide desB30 human insulin and $N^{\epsilon B29}$-$\omega$-carboxypentadecanoyl-$\gamma$-amino-butanoyl des(B30) human insulin together with suitable pharmaceutically acceptable adjuvants which composition contains between 5 and 16; 5 and 14; 5 and 12; 5 and 10; or between 5 and 8 zinc ions per 6 insulin molecules.

In a further embodiment the pharmaceutical composition comprises a fixed combination of an insulinotropic GLP-1 compound and an acylated basal insulin selected from the group consisting of $N^{\epsilon B29}$-tetradecanoyl des(B30) human insulin, $Lys^{B29}(N^{\epsilon}$ lithocholyl-$\gamma$-Glu)-des(B30) human insulin, $N^{\epsilon B29}$—($N^{\alpha}$—(HOOC(CH$_2$)$_{14}$CO)-$\gamma$-Glu) desB30 human insulin, $N^{\epsilon B29}$-$\omega$-carboxypentadecanoyl-$\gamma$-L-glutaylamide desB30 human insulin and $N^{\epsilon B29}$-$\omega$-carboxypentadecanoyl-$\gamma$-amino-butanoyl des(B30) human insulin together with suitable pharmaceutically acceptable adjuvants which composition contains between 6 and 16; 6 and 14; 6 and 12; 6 and 10; or between 6 and 8 zinc ions per 6 insulin molecules.

In a further embodiment the pharmaceutical composition comprises a fixed combination of an insulinotropic GLP-1 compound and an acylated basal insulin selected from the group consisting of $N^{\epsilon B29}$-tetradecanoyl des(B30) human insulin, $Lys^{B29}(N^{\epsilon}$ lithocholyl-$\gamma$-Glu)-des(B30) human insulin, $N^{\epsilon B29}$—($N^{\alpha}$—(HOOC(CH$_2$)$_{14}$CO)-$\gamma$-Glu) desB30 human insulin, $N^{\epsilon B29}$-$\omega$-carboxypentadecanoyl-$\gamma$-L-glutaylamide desB30 human insulin and $N^{\epsilon B29}$-$\omega$-carboxypentadecanoyl-$\gamma$-amino-butanoyl des(B30) human insulin together with suitable pharmaceutically acceptable adjuvants which composition contains between 7 and 16; 7 and 14; 7 and 12; or between 7 and 10 zinc ions per 6 insulin molecules.

In a further embodiment the pharmaceutical composition comprises a fixed combination of an insulinotropic GLP-1 compound and an acylated basal insulin selected from the group consisting of $N^{\epsilon B29}$-tetradecanoyl des(B30) human insulin, $Lys^{B29}(N^{\epsilon}$ lithocholyl-$\gamma$-Glu)-des(B30) human insulin, $N^{\epsilon B29}$—($N^{\alpha}$—(HOOC(CH$_2$)$_{14}$CO)-$\gamma$-Glu) desB30 human insulin, $N^{\epsilon B29}$-$\omega$-carboxypentadecanoyl-$\gamma$-L-glutaylamide desB30 human insulin and $N^{\epsilon B29}$-$\omega$-carboxypentadecanoyl-$\gamma$-amino-butanoyl des(B30) human insulin together with suitable pharmaceutically acceptable adjuvants which composition contains between 8 and 16; 8 and 14; 8 and 12: or between 8 and 10 zinc ions per 6 insulin molecules.

In a further embodiment the pharmaceutical composition comprises a fixed combination of an insulinotropic GLP-1 compound and an acylated basal insulin with the formula $N^{\epsilon B29}$—($N^\alpha$—(HOOC(CH$_2$)$_{14}$CO)-γ-Glu) desB30 human insulin together with suitable pharmaceutically acceptable adjuvants which composition contains at least 5, 6, 7, 8, 9, 10, 11, 12, 13, 14, 15 or 16 zinc ions per 6 insulin molecules.

In a further embodiment the pharmaceutical composition comprises a fixed combination of an insulinotropic GLP-1 compound and an acylated basal insulin $N^{\epsilon B29}$—($N^\alpha$—(HOOC(CH$_2$)$_{14}$CO)-γ-Glu) desB30 human insulin together with suitable pharmaceutically acceptable adjuvants which composition contains between 5 and 16 zinc ions per 6 insulin molecules.

In a further embodiment the pharmaceutical composition comprises a fixed combination of an insulinotropic GLP-1 compound and an acylated basal insulin $N^{\epsilon B29}$—($N^\alpha$—(HOOC(CH$_2$)$_{14}$CO)-γ-Glu) desB30 human insulin together with suitable pharmaceutically acceptable adjuvants which composition contains between 6 and 16; 6 and 15; 6 and 14; 6 and 13; 6 and 12; 6 and 10; or between 6 and 8 zinc ions per 6 insulin molecules.

In a further embodiment the pharmaceutical composition comprises a fixed combination of an insulinotropic GLP-1 compound and an acylated basal insulin $N^{\epsilon B29}$—($N^\alpha$—(HOOC(CH$_2$)$_{14}$CO)-γ-Glu) desB30 human insulin together with suitable pharmaceutically acceptable adjuvants which composition contains between 7 and 16; 7 and 15; 7 and 14; 7 and 13; 7 and 12; 7 and 11; 7 and 10; 7 and 9; or between 7 and 8 zinc ions per 6 insulin molecules.

In a further embodiment the pharmaceutical composition comprises a fixed combination of an insulinotropic GLP-1 compound and an acylated basal insulin $N^{\epsilon B29}$—($N^\alpha$—(HOOC(CH$_2$)$_{14}$CO)-γ-Glu) desB30 human insulin together with suitable pharmaceutically acceptable adjuvants which composition contains between 8 and 16; 8 and 15; 8 and 14; 8 and 13; 8 and 12; 8 and 11; 8 and 10; or between 8 and 9 zinc ions per 6 insulin molecules.

In one embodiment the invention is related to a pharmaceutical composition containing a fixed combination of an insulinotropic GLP-1 compound and a basal insulin $N^{\epsilon B29}$-tetradecanoyl des(B30) human insulin together with suitable pharmaceutically acceptable adjuvants, wherein the zinc content is at least 5, 6, 7, 8, 9, 10, 11, 12, 13, 14, 15 or 16 zinc ions per 6 insulin molecules.

In another embodiment the invention is related to a pharmaceutical composition containing a fixed combination of an insulinotropic GLP-1 compound and a basal insulin $N^{\epsilon B29}$-tetradecanoyl des(B30) human insulin together with suitable pharmaceutically acceptable adjuvants, wherein the zinc content is between 5 and 16; 6 and 16; between 7 and 16; or between 8 and 16 zinc ions per 6 insulin molecules.

In a further embodiment the pharmaceutical composition comprises a fixed combination of an GLP-1(7-37) or an analogue or derivative thereof and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω-carboxypentadecanoyl-γ-L-glutaylamide desB30 human insulin and $N^{\epsilon B29}$-ω-carboxypentadecanoyl-γ-amino-butanoyl des(B30) human insulin together with suitable pharmaceutically acceptable adjuvants which composition contains at least 5 or 6 zinc ions per 6 insulin molecules.

In a further embodiment the pharmaceutical composition comprises a fixed combination of an GLP-1(7-37) or an analogue or derivative thereof and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω-carboxypentadecanoyl-γ-L-glutaylamide desB30 human insulin and $N^{\epsilon B29}$-ω-carboxypentadecanoyl-γ-amino-butanoyl des(B30) human insulin together with suitable pharmaceutically acceptable adjuvants which composition contains between 5 and 16; 5 and 14; 5 and 12; 5 and 10 or between 5 and 8 zinc ions per 6 insulin molecules.

In a further embodiment the pharmaceutical composition comprises a fixed combination of an GLP-1(7-37) or an analogue or derivative thereof and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω-carboxypentadecanoyl-γ-L-glutaylamide desB30 human insulin and $N^{\epsilon B29}$-ω-carboxypentadecanoyl-γ-amino-butanoyl des(B30) human insulin together with suitable pharmaceutically acceptable adjuvants which composition contains between 6 and 16; 6 and 14; 6 and 12; or 6 and 10 zinc ions per 6 insulin molecules.

In a further embodiment the pharmaceutical composition comprises a fixed combination of an GLP-1(7-37) or an analogue or derivative thereof and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω-carboxypentadecanoyl-γ-L-glutaylamide desB30 human insulin and $N^{\epsilon B29}$-ω-carboxypentadecanoyl-γ-amino-butanoyl des(B30) human insulin together with suitable pharmaceutically acceptable adjuvants which composition contains between 7 and 16; 7 and 14; 7 and 12; or between 7 and 10 zinc ions per 6 insulin molecules.

In a further embodiment the pharmaceutical composition comprises a fixed combination of an GLP-1(7-37) or an analogue or derivative thereof and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω-carboxypentadecanoyl-γ-L-glutaylamide desB30 human insulin and $N^{\epsilon B29}$-ω-carboxypentadecanoyl-γ-amino-butanoyl des(B30) human insulin together with suitable pharmaceutically acceptable adjuvants which composition contains between 8 and 16; 8 and 12; or between 8 and 10 zinc ions per 6 insulin molecules.

In one embodiment the invention is related to a pharmaceutical composition containing a fixed combination of GLP-1(7-37) or an analogue or derivatives thereof and $N^{\epsilon B29}$-tetradecanoyl des(B30) human insulin together with suitable pharmaceutically acceptable adjuvants, wherein the zinc content is at least 5, 6, 7, 8, 9, or 10 zinc ions per 6 insulin molecules.

In a further embodiment the invention is related to a pharmaceutical composition containing a fixed combination of GLP-1(7-37) or an analogue or derivatives thereof and $N^{\epsilon B29}$-tetradecanoyl des(B30) human insulin together with suitable pharmaceutically acceptable adjuvants, wherein the zinc content is between 6 and 16; 7 and 16; 8 and 16; 8 and 14; 8 and 12; or between 8 and 10 zinc ions per 6 insulin molecules.

In a further embodiment the pharmaceutical composition comprises a fixed combination of Arg$^{34}$, Lys$^{26}$($N^\epsilon$-(γ-Glu($N^\alpha$-hexadecanoyl)))-GLP-1(7-37) and an acylated basal insulin selected from the group consisting of $N^{\epsilon B29}$-tetradecanoyl des(B30) human insulin, Lys$^{B29}$($N^\epsilon$ lithocholyl-γ-Glu)-des(B30) human insulin, $N^{\epsilon B29}$—($N^\alpha$—(HOOC(CH$_2$)$_{14}$CO)-γ-Glu) desB30 human insulin, $N^{\epsilon B29}$-ω- carboxypentadecanoyl-γ-L-glutaylamide desB30 human insulin and $N^{εB29}$-ω-carboxypentadecanoyl-γ-amino-butanoyl des(B30) human insulin together with suitable pharmaceutically acceptable adjuvants which composition contains at least 5, 6, 7, 8, 9, 10, 11, 12, 13, 14, 15 or 16 zinc atoms per 6 insulin molecules.

In a further embodiment the pharmaceutical composition comprises a fixed combination of $Arg^{34}$, $Lys^{26}(N^ε\text{-}(γ\text{-Glu}(N^α\text{-hexadecanoyl})))$-GLP-1(7-37) and an acylated basal insulin selected from the group consisting of $N^{εB29}$-tetradecanoyl des(B30) human insulin, $Lys^{B29}(N^ε$ lithocholyl-γ-Glu)-des(B30) human insulin, $N^{εB29}$—($N^α$—(HOOC$(CH_2)_{14}$CO)-γ-Glu) desB30 human insulin, $N^{εB29}$-ω-carboxypentadecanoyl-γ-L-glutaylamide desB30 human insulin and $N^{εB29}$-ω-carboxypentadecanoyl-γ-amino-butanoyl des(B30) human insulin together with suitable pharmaceutically acceptable adjuvants which composition contains between 5 and 16; 5 and 14; 5 and 12; or between 5 and 10 zinc ions per 6 insulin molecules.

In a further embodiment the pharmaceutical composition comprises a fixed combination of $Arg^{34}$, $Lys^{26}(N^ε\text{-}(γ\text{-Glu}(N^α\text{-hexadecanoyl})))$-GLP-1(7-37) and an acylated basal insulin selected from the group consisting of $N^{εB29}$-tetradecanoyl des(B30) human insulin, $Lys^{B29}(N^ε$ lithocholyl-γ-Glu)-des(B30) human insulin, $N^{εB29}$—($N^α$—(HOOC$(CH_2)_{14}$CO)-γ-Glu) desB30 human insulin, $N^{εB29}$-ω-carboxypentadecanoyl-γ-L-glutaylamide desB30 human insulin and $N^{εB29}$-ω-carboxypentadecanoyl-γ-amino-butanoyl des(B30) human insulin together with suitable pharmaceutically acceptable adjuvants which composition contains between 6 and 16; 6 and 14; 6 and 12; or between 6 and 10 zinc ions per 6 insulin molecules.

In a further embodiment the pharmaceutical composition comprises a fixed combination of $Arg^{34}$, $Lys^{26}(N^ε\text{-}(γ\text{-Glu}(N^α\text{-hexadecanoyl})))$-GLP-1(7-37) and an acylated basal insulin selected from the group consisting of $N^{εB29}$-tetradecanoyl des(B30) human insulin, $Lys^{B29}(N^ε$ lithocholyl-γ-Glu)-des(B30) human insulin, $N^{εB29}$—($N^α$—(HOOC$(CH_2)_{14}$CO)-γ-Glu) desB30 human insulin, $N^{εB29}$-ω-carboxypentadecanoyl-γ-L-glutaylamide desB30 human insulin and $N^{εB29}$-ω-carboxypentadecanoyl-γ-amino-butanoyl des(B30) human insulin together with suitable pharmaceutically acceptable adjuvants which composition contains between 7 and 16; 7 and 14; 7 and 12 or between 7 and 10 zinc ions per 6 insulin molecules.

In a further embodiment the pharmaceutical composition comprises a fixed combination of $Arg^{34}$, $Lys^{26}(N^ε\text{-}(γ\text{-Glu}(N^α\text{-hexadecanoyl})))$-GLP-1(7-37) and an acylated basal insulin selected from the group consisting of $N^{εB29}$-tetradecanoyl des(B30) human insulin, $Lys^{B29}(N^ε$ lithocholyl-γ-Glu)-des(B30) human insulin, $N^{εB29}$—($N^α$—(HOOC$(CH_2)_{14}$CO)-γ-Glu) desB30 human insulin, $N^{εB29}$-ω-carboxypentadecanoyl-γ-L-glutaylamide desB30 human insulin and $N^{εB29}$-ω-carboxypentadecanoyl-γ-amino-butanoyl des(B30) human insulin together with suitable pharmaceutically acceptable adjuvants which composition contains between 8 and 16; 8 and 14; 8 and 12 or between 8 and 10 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 5 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 6 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 7 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 8 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 9 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is at least 10 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is between 5 and 16; 5 and 15; 5 and 14; 5 and 13; 5 and 12; 5 and 11; 5 and 10; 5 and 9; or between 5 and 8 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is between 6 and 16; 6 and 15; 6 and 14; 6 and 13; 6 and 12; 6 and 11; or between 6 and 10 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is between 7 and 16; 7 and 15; 7 and 14; 7 and 13; 7 and 12; 7 and 11; 7 and 10; 7 and 9; or between 7 and 8 zinc ions per 6 insulin molecules.

In a further embodiment the invention is related to a pharmaceutical composition containing a fixed combination of $Arg^{34}$, $Lys^{26}(N^ε\text{-}(γ\text{-Glu}(N^α\text{-hexadecanoyl})))$-GLP-1(7-37) and $N^{εB29}$—($N^α$—(HOOC$(CH_2)_{14}$CO)-γ-Glu) desB30 human insulin together with suitable pharmaceutically acceptable adjuvants, wherein the zinc content is between 8 and 16; 8 and 15; 8 and 14; 8 and 13, 8 and 12; 8 and 11; 8 and 10; or between 8 and 9 zinc ions per 6 insulin molecules.

In a further embodiment the invention is related to a pharmaceutical composition containing a fixed combination of insulin glargine and an exendin-4 analogue, e.g. an exendin-4 analogue comprising 4-6 added Lys- or Arg-amino acid residues together with suitable pharmaceutically acceptable adjuvants, wherein the zinc content is at least above 5, 6, 7 or 8 zinc ions per 6 insulin molecules. In this embodiment the insulin glargine may also be an amidated insulin glargine as disclosed in WO2008/006496 and WO2008/006497.

The pH may in any of the above embodiment be 7.4; 7.5; 7.6; 7.8; 7.9; 8; 8.1; 8.2; 8.3; 8.4 or 8.5. In another embodiment the pH is between 7.4 and 8.2 or between 7.5 and 8. In still another embodiment, the pH is between 7.6 and 8.

If the GLP-1 compound is $Arg^{34}$, $Lys^{26}(N^{\epsilon}$-($\gamma$-Glu($N^{\alpha}$-hexadecanoyl)))-GLP-1(7-37) the pH will typically be between about 7.7 and about 8.2.

A further aspect of the present invention is related to a method for preparation of a pharmaceutical composition according to any one of the above embodiments comprising dissolving said basal insulin and admixing it with a preservative and an isotonicity modifier, then adding zinc and finally admixing with the dissolved insulinotropic peptide.

One embodiment the method according to the invention comprises the following steps: 1) dissolving the basal insulin in a water solution of buffer and isotonicity agent, 2) adding of zinc optionally stepwise, 3) adjusting pH, 4) storing the solution at a temperature between about 4-5° C. and ambient temperature and 5) adding the GLP-1 compound.

In a further aspect the present invention is related to a method for the treatment of hyperglycemia comprising parenteral administration of an effective amount of the pharmaceutical composition according to any one of the above embodiments to a mammal in need of such treatment.

In a further aspect the present invention is related to a method for the treatment of obesity, beta-cell deficiency, IGT or dyslipidemia comprising parenteral administration of an effective amount of the pharmaceutical composition according to any one of the above embodiments to a mammal in need of such treatment.

Another aspect of the present invention is related to the use of a shelf-stable pharmaceutical composition comprising a mixture of an insulinotropic GLP-1 compound and a basal insulin which composition contains at least 6 zinc atoms per 6 insulin molecules for the treatment of hyperglycemia by parenteral administration.

In another aspect the invention is related to a method for weight reduction comprising administrating an effective amount of a pharmaceutical composition comprising a mixture of an insulinotropic GLP-1 compound and a basal insulin which composition contains at least 6 zinc atoms per 6 insulin molecules.

DESCRIPTION OF THE INVENTION

This invention relates to the administration of a fixed mixture of a basal insulin and an insulinotropic GLP-1 compound for diabetes type 2 patients. When a GLP-1 compound and a basal insulin is combined in a single formulation, the patients save one injection compared to the two separate injections required for administrating the two components separately and more importantly, a number of positive synergetic effects are expected when administrating both a basal insulin analogue and a GLP-1 compound at the same time.

In such mixture the individual active component, the basal insulin and the GLP-1 compound, should keep their attractive PK profile known from mono treatment. For example the basal insulin analogue insulin $N^{\epsilon B29}$—($N^{\alpha}$—(HOOC($CH_2)_{14}CO$)-$\gamma$-Glu) desB30 human insulin has an attractive profile suited for once-daily administration. Likewise, the GLP-1 analogue $Arg^{34}$, $Lys^{26}(N^{\epsilon}$-($\gamma$-Glu($N^{\alpha}$-hexadecanoyl)))-GLP-1(7-37) is administrated once daily. Hence, the combination of insulin $N^{\epsilon B29}$—($N^{\alpha}$—(HOOC($CH_2)_{14}CO$)-$\gamma$-Glu) desB30 human insulin and liraglutide constitutes an attractive combination of a basal insulin analogue and a GLP-1 analogue.

However, immediate mixing of acylated insulin analogues such as $N^{\epsilon B29}$—($N^{\alpha}$—(HOOC($CH_2)_{14}CO$)-$\gamma$-Glu) desB30 human insulin with a GLP-1 compound such as $Arg^{34}$, $Lys^{26}(N^{\epsilon}$-($\gamma$-Glu($N^{\alpha}$-hexadecanoyl)))-GLP-1(7-37) results in both a physically less stable formulation and in altered PK properties of the acylated insulin. A commercial formulation however has to have a high physical stability. Also, if the PK properties of the basal insulin are altered too much it may result in loss of its 24 hours coverage.

Most basal insulins will be formulated with zinc to have a satisfactory PK and physical stability. For example it has been shown that $N^{\epsilon B29}$—($N^{\alpha}$—(HOOC($CH_2)_{14}CO$)-$\gamma$-Glu) desB30 human insulin is able to bind more than the traditional 2-3 zinc ions per 6 insulin. An additional 2-3 zinc ions (a total of 5-6 zinc ions per 6 insulin molecules) are required for $N^{\epsilon B29}$—($N^{\alpha}$—(HOOC($CH_2)_{14}CO$)-$\gamma$-Glu) desB30 human insulin to have an optimal once-daily profile.

We have found that $Arg^{34}$, $Lys^{26}(N^{\epsilon}$-($\gamma$-Glu($N^{\alpha}$-hexadecanoyl)))-GLP-1(7-37) has a low affinity zinc binding and that both the physical instability and the PK properties of the $N^{\epsilon B29}$—($N^{\alpha}$—(HOOC($CH_2)_{14}CO$)-$\gamma$-Glu) desB30 human insulin are influenced by this in a mixture of the two component. In a mixture of $Arg^{34}$, $Lys^{26}(N^{\epsilon}$-($\gamma$-Glu($N^{\alpha}$-hexadecanoyl)))-GLP-1(7-37) and $N^{\epsilon B29}$—($N^{\alpha}$—(HOOC($CH_2)_{14}CO$)-$\gamma$-Glu) desB30 human insulin it is in the binding of these additional zinc ions that $Arg^{34}$, $Lys^{26}(N^{\epsilon}$-($\gamma$-Glu($N^{\alpha}$-hexadecanoyl)))-GLP-1(7-37) competes with insulin $N^{\epsilon B29}$—($N^{\alpha}$—(HOOC($CH_2)_{14}CO$)-$\gamma$-Glu) desB30 human insulin.

We have found that adding further zinc ions to the mixture of $N^{\epsilon B29}$—($N^{\alpha}$—(HOOC($CH_2)_{14}CO$)-$\gamma$-Glu) desB30 human insulin with $Arg^{34}$, $Lys^{26}(N^{\epsilon}$-($\gamma$-Glu($N^{\alpha}$-hexadecanoyl)))-GLP-1(7-37) improves the physical stability and improves the PK profile of the $N^{\epsilon B29}$—($N^{\alpha}$—(HOOC($CH_2)_{14}CO$)-$\gamma$-Glu) desB30 human insulin towards the desired profile obtained with 5-6 zinc ions per insulin molecule for insulin $N^{\epsilon B29}$—($N^{\alpha}$—(HOOC($CH_2)_{14}CO$)-$\gamma$-Glu) desB30 human insulin alone.

The term "GLP-1 compound" as used herein means GLP-1(7-37), insulinotropic analogues thereof and insulinotropic derivatives thereof. GLP-1 compounds also include exendin compounds such as exendin-3 and exendin-4 and analogues thereof such as ZP10 or ZP10A which is an exendin-4 analogue with 6 added lysine residues to the C-terminal end of the molecule, see Cristian Thorkildsen et al, The Journal of Pharmacology and Experimental Therapeutics, Vol 307, No. 2 (2003), 490-496.

An embodiment of the invention comprises a pharmaceutical composition according to any of the above embodiments, wherein the insulinotropic GLP-1 peptide is acylated exendin-4 or an acylated exendin-4 analogue such as [N-epsilon(17-carboxyheptadecanoic acid)20 exendin-4(1-39)-amide and N-epsilon32-(17-carboxy-heptadecanoyl)[Lys32] exendin-4(1-39)amide.

A simple system is used to describe fragments and analogues of GLP-1. Thus, for example, $Gly^8$-GLP-1(7-37) designates an analogue of GLP-1(7-37) formally derived from GLP-1(7-37) by substituting the naturally occurring amino acid residue in position 8 (Ala) by Gly. Similarly, $Lys^{34}(N^{\epsilon}$-tetradecanoyl)-GLP-1(7-37) designates GLP-1(7-37)

wherein the ε-amino group of the Lys residue in position 34 has been tetradecanoylated. PCT publications WO 98/08871 and WO 99/43706 disclose stable derivatives of GLP-1 analogues, which have a lipophilic substituent. These stable derivatives of GLP-1 analogues have a protracted profile of action compared to the corresponding GLP-1 analogues.

The term "insulinotropic" as used herein referring to a peptide or a compound means the ability to stimulate secretion of insulin in response to an increased plasma glucose level. Insulinotropic peptides and compounds are agonists of the GLP-1 receptor. The insulinotropic property of a compound may be determined by in vitro or in vivo assays known in the art.

In one embodiment of the invention the GLP-1 has an Arg residue in position 34. In another embodiment the GLP-1 has Glu residue in position 22. In another embodiment of the invention the GLP-1 has an L-histidine residue in position 8. In another embodiment of the invention the GLP-1 has a Val residue in position 8. In another embodiment of the invention the derivative of a GLP-1(7-37) analogue is GLP-1(7-36)-amide.

In one embodiment of the invention the GLP-1(7-37) analogue is selected from the group consisting of GLP-1(7-36) amide, $Arg^{34}$-GLP-1(7-37), $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{16}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37).

In another embodiment the present invention the insulinotropic peptide is a derivative of GLP-1(7-37) or a derivative of a GLP-1(7-37) analogue having a lysine residue, such as one lysine, wherein a lipophilic substituent optionally via a spacer is attached to the epsilon amino group of said lysine. In one embodiment of the invention said lipophilic substituent has from 8 to 40 carbon atoms, preferably from 8 to 24, eg 12-18. In another embodiment of the invention said spacer is present and is selected from an amino acid, eg. beta-Ala, L-Glu, aminobutyroyl. In another embodiment of the invention said insulinotropic peptide is a dipeptidyl aminopeptidase IV protected GLP-1 compound. In another embodiment of the invention said insulinotropic peptide is a plasma stable GLP-1 compound. In another embodiment of the invention said derivative of a GLP-1(7-37) analogue is $Arg^{34}$, $Lys^{26}(N^\epsilon$-(γ-Glu($N^\alpha$-hexadecanoyl)))-GLP-1(7-37). Non-limiting examples of GLP-1 derivatives are desamino-$His^7$, $Arg^{26}$, $Lys^{34}(N^\epsilon$-(γ-Glu($N^\alpha$-hexadecanoyl)))-GLP-1(7-37), desamino-$His^7$, $Arg^{26}$, $Lys^{34}(N^\epsilon$-octanoyl)-GLP-1(7-37), $Arg^{26,34}$, $Lys^{38}(N^\epsilon$-(ω-carboxypentadecanoyl))-GLP-1(7-38), $Arg^{26,34}$, $Lys^{36}(N^\epsilon$-(γ-Glu($N^\alpha$-hexadecanoyl)))-GLP-1 (7-36) and $Arg^{34}$, $Lys^{26}(N^\epsilon$-(γ-Glu($N^\alpha$-hexadecanoyl)))-GLP-1(7-37). Non-limiting examples of GLP-1 derivatives are desamino-$His^7$, $Arg^{26}$, $Lys^{34}(N^\epsilon$-(γ-Glu($N^\alpha$-hexadecanoyl)))-GLP-1(7-37), desamino-$His^7$, $Arg^{26}$, $Lys^{34}$ ($N^\epsilon$-octanoyl)-GLP-1(7-37), $Arg^{26,34}$, $Lys^{36}(N^\epsilon$-(ω-carboxypentadecanoyl)))-GLP-1 (7-38), $Arg^{26,34}$, $Lys^{36}(N^\epsilon$-(γ-Glu($N^\alpha$-hexadecanoyl)))-GLP-1 (7-36) and $Arg^{34}$, $Lys^{26}(N^\epsilon$-(γ-Glu($N^\alpha$-hexadecanoyl)))-GLP-1(7-37).

In another embodiment the GLP-1 analogue is a further protracted analogue of the type disclosed in WO 2006/097537, such as Aib8,Lys26(OEG-OEG-gamma-Glu-C18-diacid),Arg34)GLP-1(7-37), N-$\epsilon^{26}$-(17-carboxyheptadecanoyl)-[Aib8,Arg34]GLP-1-(7-37)-peptide,N-$\epsilon^{26}$-(19-carboxynonadecanoyl)-[Aib8,Arg34]GLP-1-(7-37)-peptide, N-$\epsilon^{26}$-(4-{[N-(2-carboxyethyl)-N-(15-carboxypentadecanoyl)amino]methyl}benzoyl)[Arg34] GLP-1-(7-37), N-$\epsilon^{26}$-[2-(2-[2-(2-[2-(2-[4-(17-Carboxyheptadecanoylamino)-4(S)-carboxybutyrylamino] ethoxy)ethoxy]acetylamino)ethoxy]ethoxy)acetyl][Aib8, Arg34]GLP-1-(7-37)peptide, In one embodiment the GLP1-derivative is Aib8,Lys26 (OEG-OEG-gamma-Glu-C18-diacid),Arg34)GLP-1(7-37). Its higher potency compared to $Arg^{34}$, $Lys^{26}(N^\epsilon$-(γ-Glu($N^\alpha$-hexadecanoyl)))-GLP-1(7-37) and the lower dose required for once-daily rather than once-weekly dosing will result in a lower concentration of the GLP-1 compound needed in a combination formulation with the basal insulin.

The basal insulin may be an acylated soluble insulin as disclosed in WO 95/07931, WO 2005/012347 or EP2007/054444.

Acylated basal insulin may be selected from the following list:

$N^{\epsilon B29}$-tridecanoyl des(B30) human insulin,
$N^{\epsilon B29}$-tetradecanoyl des(B30) human insulin,
$N^{\epsilon B29}$-decanoyl des(B30) human insulin,
$N^{\epsilon B29}$-dodecanoyl des(B30) human insulin,
$N^{\epsilon B29}$—($N^\alpha$—(HOOC(CH$_2$)$_{14}$CO)-γ-Glu) des(B30) human insulin;
$N^{\epsilon B29}$—($N^\alpha$—(HOOC(CH$_2$)$_{15}$CO)-γ-Glu) des(B30) human insulin;
$N^{\epsilon B29}$—($N^\alpha$—(HOOC(CH$_2$)$_{16}$CO)-γ-Glu) des(B30) human insulin;
$N^{\epsilon B29}$—($N^\alpha$—(HOOC(CH$_2$)$_{17}$CO)-γ-Glu) des(B30) human insulin;
$N^{\epsilon B29}$—($N^\alpha$—(HOOC(CH$_2$)$_{18}$CO)-γ-Glu) des(B30) human insulin;
$N^{\epsilon B29}$—($N^\alpha$—(HOOC(CH$_2$)$_{16}$CO)-γ-Glu-$N^\alpha$-(γ-Glu)) des(B30) human insulin;
$N^{\epsilon B29}$—($N^\alpha$-(Asp-OC(CH$_2$)$_{16}$CO)-γ-Glu) des(B30) human insulin;
$N^{\epsilon B29}$—($N^\alpha$-(Glu-OC(CH$_2$)$_{14}$CO)-γ-Glu) des(B30) human insulin;
$N^{\epsilon B29}$—($N^\alpha$-(Glu-OC(CH$_2$)$_{14}$CO—) des(B30) human insulin;
$N^{\epsilon B29}$—($N^\alpha$-(Asp-OC(CH$_2$)$_{16}$CO—) des(B30) human insulin;
$N^{\epsilon B29}$—($N^\alpha$—(HOOC(CH$_2$)$_{16}$CO)-α-Glu-$N^\alpha$-(β-Asp)) des(B30) human insulin;
$N^{\epsilon B29}$—($N^\alpha$-(Gly-OC(CH$_2$)$_{13}$CO)-γ-Glu) des(B30) human insulin;
$N^{\epsilon B29}$—($N^\alpha$-(Sar-OC(CH$_2$)$_{13}$CO)-γ-Glu) des(B30) human insulin,
$N^{\epsilon B29}$-ω-carboxy-pentadecanoyl-γ-L-glutamylamide desB30 human insulin,
$N^{\epsilon B29}$-ω-carboxy-pentadecanoyl-γ-amino-butanoyl desB30 human insulin,
$N^{\epsilon B29}$-ω-carboxy-tetradecanoyl-γ-L-glutamylamide desB30 human insulin,
$N^{\epsilon B29}$-ω-carboxy-tridecanoyl-γ-L-glutamylamide desB30 human insulin,
$N^{\epsilon B29}$-ω-carboxy-pentadecanoyl-β-alanyl desB30 human insulin,
$N^{\epsilon B29}$-ω-carboxy-pentadecanoyl-γ-L-aspartylamide desB30 human insulin, $N^{\epsilon B29}$-ω-carboxy-pentadecanoyl-ε-aminohexanoyl desB30 human insulin, $N^{\epsilon B29}$-ω-carboxy-pentadecanoyl-δ-aminopentanoyl desB30 human insulin, $N^{\epsilon B29}$-10-(4-carboxyphenoxy)-decanoyl-γ-L-glutamylamide desB30 human insulin, $N^{\epsilon B29}$-4-[11-(4-Carboxyphenyl)undecanoylamino]butyryl desB30 human insulin, $N^{\epsilon B29}$-(3-(3-{4-[3-(7-carboxyheptanoylamino)propoxy]butoxy}propylcarbamoyl)-propionyl-γ-glutamylamide) desB30 human Insulin, $N^{\epsilon B29}$-ω-carboxy-tridecanoyl-γ-amino-butanoyl desB30 human insulin, $N^{\epsilon B29}$-ω-carboxy-undecanoyl-γ-amino-butanoyl desB30 human insulin, $N^{\epsilon B29}$-ω-carboxy-tetradecanoyl-γ-amino-butanoyl desB30 human insulin, $N^{\epsilon B29}$-{4-[10-(4-Carboxy-phenoxy)-decanoylamino]-butyryl} desB30 insulin, $N^{\epsilon B29}$-{4-[(14-Carboxy-tetradecanoylamino)-methyl]-benzoyl} desB30 insulin, $N^{\epsilon B29}$-[16-(4-Carboxy-phenoxy)-hexadecanoyl] desB30 insulin, $N^{\epsilon B29}$-{4-[(15-carboxypentadecanoylamino)benzoyl]-desB30 human insulin and $N^{\epsilon B29}$-{4-[(15-Carboxy-pentadecanoylamino)-methyl]-benzoyl}-desB30 insulin.

The concentration of the GLP-1 compound in the pharmaceutical composition according to the invention may be between about 1 and 25, between about 2 and about 15, between about 2 and about 10, between about 2 and about 8 or between about 2 and about 6 mg/mL.

The concentration of the basal insulin will be between about 1 and about 25, between about 1.5 and about 15, between about 1.5 and about and 12; between about 1.5 and 8; between about 2 and about 15, between about 2 and about 10, between about 2 and about 8; between 2 and about 7; and between about 3 and 6 mg/mL.

In one embodiment the concentration of the basal insulin will be 2 mg/mL.

In another embodiment the concentration of the basal insulin will be 4 mg/mL.

In another embodiment the concentration of the basal insulin will be 8 mg/mL.

In one embodiment of the invention the concentration of $Arg^{34}$, $Lys^{26}(N^\epsilon$-(γ-Glu($N^\alpha$-hexadecanoyl)))-GLP-1(7-37) is in the range from about 2 mg/mL to about 10 mg/mL and the concentration of basal insulin is in the range from about 3 mg/mL to about 5 mg/mL.

In another embodiment of the invention the concentration of $Arg^{34}$, $Lys^{26}(N^\epsilon$-(γ-Glu($N^\alpha$-hexadecanoyl)))-GLP-1(7-37) is in the range from about 2 mg/mL to about 10 mg/mL and the concentration of basal insulin is in the range from about 7 mg/mL to about 9 mg/mL.

When mixing the combination formulations the order of adding each single component is important. As the first step water, buffer (if different from phosphate buffer), isotonicity modifier are mixed. Then an appropriate amount of the basal insulin analogue stock solution is added and gently mixed. Thereafter the preservative, e.g. phenol is added and the mixture is gently mixed for about 15-60 minutes. As the next step part of the zinc is added in an amount corresponding to a concentration of 3 zinc ions per 6 insulin molecules. The mixture is then gently mixed for at least 5 minutes. As the next step the remaining amount of zinc ions is added to the desired concentration. Then pH adjusted if it is outside the desired pH range. Then an appropriate amount of the GLP-1 compound stock solution is added to reach the desired final concentration and pH is adjusted to the desired value.

In one embodiment of the process for preparing the pharmaceutical composition the preservative is added before adding any zinc to the mixture. Thus in one embodiment the order of adding the individual components is: 1) basal insulin, 2) preservative, 3) zinc and 4) GLP-1 compound. In one embodiment the zinc is added in several steps e.g. up 3-4 steps.

Physical stability was assessed by Thioflavin T fibrillation assays and by the rotation test of Penfill.

Zinc binding by the GLP-1 compound was studied using 1D H-NMR.

The self-association equilibrium of the insulin in the absence and presence of GLP-1 compound and in the presence of increasing zinc concentration was studied using a size exclusion chromatography method with fluorescence detection (for identifying the GLP-1 compound in the chromatogram).

PK properties of combination formulations were assessed using standard appearance pig models.

The pharmaceutical composition according to the invention will in addition to the active components contain the usual pharmaceutically acceptable adjuvants such as an isotonicity agent, a buffer, a preservative and a stabilizer.

Pharmaceutically acceptable preservatives are preservative selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof.

In one embodiment the preservative is a mixture of phenol and m-cresol. In another embodiment the preservative is phenol. The use of a preservative in pharmaceutical compositions is well-known to the skilled person. For convenience reference is made to Remington: *The Science and Practice of Pharmacy*, 19$^{th}$ edition, 1995.

The formulation according to the present invention will typically comprise an isotonic agent such as mannitol, sorbitol, glycerol, propylene glycol or a mixture thereof. In one embodiment the isotonicity agent is not a salt. The use of an isotonic agent in pharmaceutical compositions is well-known to the skilled person. For convenience reference is made to Remington: *The Science and Practice of Pharmacy*, 19$^{th}$ edition, 1995.

The pharmaceutical composition according to the invention may also comprise a buffer. The buffer may be selected from a buffer which is a zwitterionic buffer, glycyl-glycine, TRIS, bicine, HEPES, MOBS, MOPS, TES and mixtures thereof. Further suitable buffers are sodium acetate, sodium carbonate, citrate, histidine, glycine, lysine, arginine, sodium dihydrogen phosphate, disodium hydrogen phosphate, sodium phosphate, and tris(hydroxymethyl)-aminomethan, tricine, malic acid, succinate, maleic acid, fumaric acid, tartaric acid, aspartic acid or mixtures thereof.

The pharmaceutical formulation according to the present invention will preferably not contain a zinc binding buffer such as a phosphate buffer.

The composition may also comprise a zinc chelating compound, which may act as a zinc buffer for free zinc ions in the formulations. This will enable an increased zinc concentration with relative lower liraglutide diheptamer formation. Such zinc chelating compounds may include (but not limited to), histidine, imidazole, citrate or derivatives hereof.

In one embodiment the zinc chelator is histidine.

In another embodiment the zinc chelator is imidazole.

The addition of such a zinc chelator is preferably below 10 mM, more preferably below 5 mM, more preferably below 2 mM, more preferably below 1 mM, more preferably below 0.5 mM.

The term "shelf-stable pharmaceutical composition" as used herein means a pharmaceutical composition which is stable for at least the period which is required by regulatory agencies in connection with therapeutic proteins. Preferably, a shelf-stable pharmaceutical composition is stable for at least one year at 5° C. Stability includes chemical stability as well as physical stability.

The term "basal insulin" as used herein means an insulin peptide which has a time-action of more than 8 hours in standard models of diabetes. Preferably, the basal insulin has a time-action of at least 9 hours. Preferably, the basal insulin has a time-action of at least 10 hours. Preferably, the basal meal-related insulin has a time-action in the range from 9 to 15 hours. Preferably, the meal-related insulin has a time-action similar to that observed for commercial pharmaceutical compositions of NPH insulin and $N^{\epsilon B29}$-tetradecanoyl des(B30) human insulin.

The term "effective amount" as used herein means a dosage which is sufficient in order for the treatment of the patient to be effective compared with no treatment.

The term "pharmaceutically acceptable" as used herein means suited for normal pharmaceutical applications, i.e. giving rise to no adverse events in patients etc.

The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycine and sodium citrate.

The term "preservative" as used herein refers to a chemical compound which is added to a pharmaceutical composition to prevent or delay microbial activity (growth and metabolism).

The term "isotonicity agent" as used refers to a chemical compound in a pharmaceutical composition that serves to modify the osmotic pressure of the pharmaceutical composition so that the osmotic pressure becomes closer to that of human plasma. Isotonicity agents include NaCl, glycerol, mannitol etc.

The term "stabilizer" as used herein refers to chemicals added to peptide containing pharmaceutical compositions in order to stabilize the peptide, i.e. to increase the shelf life and/or in-ude time of such compositions. Examples of stabilizers used in pharmaceutical formulations are L-glycine, L-histidine, arginine, polyethylene glycol, and carboxymethylcellulose.

The term "insulin peptide" as used herein means a peptide which is either human insulin or an analog or a derivative thereof with insulin activity.

The term "human insulin" as used herein means the human hormone whose structure and properties are well known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide.

The insulin analogues will typically not comprise more than about 7 mutations, more typically not more than 5 and even more typically at the most 3 mutations compared to human insulin.

Over the years a fairly large number of modification of the insulin A- and or B-chain have been disclosed. Thus the position 28 of the B chain may be modified from the natural Pro residue to Asp, Lys, or Ile and Lys in position B29 may also be modified to Pro.

Also, Asn at position A21 may be modified to Ala, Gln, Glu, Gly, His, Ile, Leu, Met, Ser, Thr, Trp, Tyr or Val, in particular to Gly, Ala, Ser, or Thr and in particular to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Also, the natural amino acid residue in position A18 may be changed to a Gln residue or one or more of the amino acid residue in positions B26-B30 may be deleted.

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, PEGylations and the like. Examples of derivatives of human insulin are threonine methyl ester$^{B30}$ human insulin and $N^{\epsilon B29}$-tetradecanoyl des(B30) human insulin.

The term "isoelectric point" as used herein means the pH value where the overall net charge of a macromolecule such as a peptide is zero. In peptides there may be several charged groups, and at the isoelectric point the sum of all these charges is zero. At a pH above the isoelectric point the overall net charge of the peptide will be negative, whereas at pH values below the isoelectric point the overall net charge of the peptide will be positive.

The term "about" as used herein in relation to the concentration of a peptide in a pharmaceutical composition means plus or minus 10%. Hence, the concentration "about 5 mg/mL insulin" means a concentration of 4.5 mg/mL insulin to 5.5 mg/mL insulin.

The invention covers the following embodiments:

Embodiment 1

A soluble pharmaceutical composition for parenteral administration which comprises an insulinotropic GLP-1 compound, a basal insulin peptide, pharmaceutically acceptable additives and zinc, wherein the zinc content is at least 5 Zn ions per 6 insulin molecules.

Embodiment 2

A soluble pharmaceutical composition for parenteral administration according to embodiment 1, which comprises an insulinotropic GLP-1 compound, a basal insulin peptide, pharmaceutically acceptable additives and zinc, wherein the zinc content is at least 6 Zn ions per 6 insulin molecules.

Embodiment 3

The pharmaceutical composition according to embodiment 1, wherein the zinc content is between 5 and 16 zinc ions per 6 insulin molecules.

Embodiment 4

The pharmaceutical composition according to embodiment 1, wherein the zinc content is between 5 and 15 zinc ions per 6 insulin molecules.

Embodiment 5

The pharmaceutical composition according to embodiment 1, wherein the zinc content is between 5 and 14 zinc ions per 6 insulin molecules.

Embodiment 6

The pharmaceutical composition according to embodiment 1, wherein the zinc content is between 5 and 13 zinc ions per 6 insulin molecules.

Embodiment 7

The pharmaceutical composition according to embodiment 1, wherein the zinc content is between 5 and 12 zinc ions per 6 insulin molecules.

Embodiment 8

The pharmaceutical composition according to embodiment 1, wherein the zinc content is between 5 and 11 zinc ions per 6 insulin molecules.

Embodiment 9

The pharmaceutical composition according to embodiment 1, wherein the zinc content is between 5 and 10 zinc ions per 6 insulin molecules.

Embodiment 10

The pharmaceutical composition according to embodiment 1, wherein the zinc content is between 5 and 9 zinc ions per 6 insulin molecules.

Embodiment 11

The pharmaceutical composition according to embodiment 1, wherein the zinc content is between 5 and 8 zinc ions per 6 insulin molecules.

Embodiment 12

The pharmaceutical composition according to embodiment 1, wherein the zinc content is between 5 and 7 zinc ions per 6 insulin molecules.

Embodiment 13

The pharmaceutical composition according to embodiment 2, wherein the zinc content is between 6 and 16 zinc ions per 6 insulin molecules.

Embodiment 14

The pharmaceutical composition according to embodiment 2, wherein the zinc content is between 6 and 15 zinc ions per 6 insulin molecules.

Embodiment 15

The pharmaceutical composition according to embodiment 2, wherein the zinc content is between 6 and 14 zinc ions per 6 insulin molecules.

Embodiment 16

The pharmaceutical composition according to embodiment 2, wherein the zinc content is between 6 and 13 zinc ions per 6 insulin molecules.

Embodiment 17

The pharmaceutical composition according to embodiment 2, wherein the zinc content is between 6 and 12 zinc ions per 6 insulin molecules.

Embodiment 18

The pharmaceutical composition according to embodiment 2, wherein the zinc content is between 6 and 11 zinc ions per 6 insulin molecules.

Embodiment 19

The pharmaceutical composition according to embodiment 2, wherein the zinc content is between 6 and 10 zinc ions per 6 insulin molecules.

Embodiment 20

The pharmaceutical composition according to embodiment, 2, wherein the zinc content is between 6 and 9 zinc ions per 6 insulin molecules.

Embodiment 21

The pharmaceutical composition according to embodiment 2, wherein the zinc content is between 6 and 8 zinc ions per 6 insulin molecules.

Embodiment 22

The pharmaceutical composition according to any of the preceding embodiments, wherein the zinc content is between 7 and 16 zinc ions per 6 insulin molecules.

Embodiment 23

The pharmaceutical composition according to any of the preceding embodiments, wherein the zinc content is between 7 and 15 zinc ions per 6 insulin molecules.

Embodiment 24

The pharmaceutical composition according to any of the preceding embodiments, wherein the zinc content is between 7 and 14 zinc ions per 6 insulin molecules.

Embodiment 25

The pharmaceutical composition according to any of the preceding embodiments, wherein the zinc content is between 7 and 13 zinc ions per 6 insulin molecules.

Embodiment 26

The pharmaceutical composition according to any of the preceding embodiments, wherein the zinc content is between 7 and 12 zinc ions per 6 insulin molecules.

Embodiment 27

The pharmaceutical composition according to any of the preceding embodiments, wherein the zinc content is between 7 and 11 zinc ions per 6 insulin molecules.

Embodiment 28

The pharmaceutical composition according to any of the preceding embodiments, wherein the zinc content is between 7 and 10 zinc ions per 6 insulin molecules.

Embodiment 29

The pharmaceutical composition according to any of the preceding embodiments, wherein the zinc content is between 7 and 9 zinc ions per 6 insulin molecules.

Embodiment 30

The pharmaceutical composition according to any of the preceding embodiments, wherein the zinc content is between 8 and 16 zinc ions per 6 insulin molecules.

Embodiment 31

The pharmaceutical composition according to any of the preceding embodiments, wherein the zinc content is between 8 and 15 zinc ions per 6 insulin molecules.

Embodiment 32

The pharmaceutical composition according to any of the preceding embodiments, wherein the zinc content is between 8 and 14 zinc ions per 6 insulin molecules.

Embodiment 33

The pharmaceutical composition according to any of the preceding embodiments, wherein the zinc content is between 8 and 13 zinc ions per 6 insulin molecules.

Embodiment 34

The pharmaceutical composition according to any of the preceding embodiments, wherein the zinc content is between 8 and 12 zinc ions per 6 insulin molecules.

Embodiment 35

The pharmaceutical composition according to any of the preceding embodiments, wherein the zinc content is between 8 and 11 zinc ions per 6 insulin molecules.

Embodiment 36

The pharmaceutical composition according to any of the preceding embodiments, wherein the zinc content is between 8 and 10 zinc ions per 6 insulin molecules.

Embodiment 37

The pharmaceutical composition according to any of the preceding embodiments, wherein the pH of said pharmaceutical composition from about pH 7.4 to about pH 9.

Embodiment 38

The pharmaceutical composition according to any of the preceding embodiments, wherein the pH of said pharmaceutical composition from about pH 7.4 to about pH 8.2.

Embodiment 39

The pharmaceutical composition according to any of the preceding embodiments, wherein the pH of said pharmaceutical composition from about pH 7.4 to about pH 7.7.

Embodiment 40

The pharmaceutical composition according to any of the preceding embodiments, wherein the pH of said pharmaceutical composition from about pH 7.6 to about pH 8.2.

Embodiment 41

The pharmaceutical composition according to any of the preceding embodiments, wherein the pH of said pharmaceutical composition from about pH 7.7 to about pH 8.2.

Embodiment 42

The pharmaceutical composition according to any of the preceding V embodiments wherein the pH of said pharmaceutical composition from about pH 8.0 to about pH 9.

Embodiment 43

The pharmaceutical composition according to any of the preceding embodiments, wherein the insulinotropic GLP-1 peptide is GLP-1(7-37), a GLP-1(7-37) analogue, a derivative of GLP-1(7-37), or a derivative of a GLP-1(7-37) analogue.

Embodiment 44

The pharmaceutical composition according to any of the preceding embodiments, wherein the derivative of GLP-1(7-37) comprises a lysine residue.

Embodiment 45

The pharmaceutical composition according to embodiment 44, wherein said derivative of a GLP-1(7-37) analogue is $Arg^{34}$, $Lys^{26}(N^{\epsilon}\text{-}(\gamma\text{-}Glu(N^{\alpha}\text{-}hexadecanoyl)))\text{-}GLP\text{-}1(7\text{-}37)$.

Embodiment 46

The pharmaceutical composition according to embodiment 44, wherein said derivative of a GLP-1(7-37) analogue is Aib8,Lys26(OEG-OEG-gamma-Glu-C18-diacid),Arg34) GLP-1 (7-37).

Embodiment 47

The pharmaceutical composition according to embodiment 44, wherein said derivative of a GLP-1(7-37) analogue is [desaminoHis$^7$,Arg$^{34}$]GLP-1-(7-37), [Aib$^8$,Glu$^{22}$,Arg$^{26}$, Arg$^{34}$,Lys$^{37}$]GLP-1-(7-37)amide.

Embodiment 48

The pharmaceutical composition according to any of the preceding embodiments 1-42, wherein the insulinotropic GLP-1 peptide is exendin-4 or an analogue thereof.

Embodiment 49

The pharmaceutical composition according to any one of the preceding embodiments, wherein the basal insulin peptide is an acylated insulin.

Embodiment 50

A pharmaceutical composition according to any one of the preceding embodiments, wherein the acylated insulin is acylated in position B29 with a lipophilic group.

Embodiment 51

The pharmaceutical composition according to embodiment 50, wherein the lipophilic group has from 8 to 40, 8 to 24, or 12-18 carbon atoms.

Embodiment 52

A pharmaceutical composition according to embodiment 50, wherein the basal insulin is selected from the group consisting of N$^{\epsilon B29}$-tetradecanoyl des(B30) human insulin, N$^{\epsilon B29}$—(N$^\alpha$—(HOOC(CH$_2$)$_{14}$CO)-γ-Glu) desB30 human insulin, Lys$^{B29}$(N$^\epsilon$ lithocholyl-γ-Glu)-des(B30) human insulin, N$^{\epsilon B29}$-ω-carboxypentadecanoyl-γ-L-glutaylamide desB30 human insulin and N$^{\epsilon B29}$-ω-carboxypentadecanoyl-γ-amino-butanoyl des(B30) human insulin.

Embodiment 53

A pharmaceutical composition according to embodiment 50, wherein the basal insulin is N$^{\epsilon B29}$-tetradecanoyl des(B30) human insulin, N$^{\epsilon B29}$—(N$^\alpha$-(HOOC(CH$_2$)$_{14}$CO)-γ-Glu) desB30 human insulin.

Embodiment 54

A pharmaceutical composition according to embodiment 50, wherein the basal insulin is N$^{\epsilon B29}$—(N$^\alpha$—(HOOC(CH$_2$)$_{14}$CO)-γ-Glu) desB30 human insulin.

Embodiment 55

A pharmaceutical composition according to embodiment 50, wherein the basal insulin is N$^{\epsilon B29}$-ω-carboxypentadecanoyl-γ-L-glutaylamide desB30 human insulin or N$^{\epsilon B29}$-ω-carboxypentadecanoyl-γ-amino-butanoyl des(B30) human insulin.

Embodiment 56

The pharmaceutical composition according to any one of the preceding embodiments 1-42, wherein the basal insulin is N$^{\epsilon B29}$—(N$^\alpha$—(HOOC(CH$_2$)$_{14}$CO)-γ-Glu) desB30 human insulin and the insulinotropic GLP-1 compound is Arg$^{34}$, Lys$^{26}$(N$^\epsilon$-(γ-Glu(N$^\alpha$-hexadecanoyl)))-GLP-1(7-37).

Embodiment 57

The pharmaceutical composition according to any of the preceding embodiments, wherein the concentration of the basal insulin is in the range from about 1.5 to about 8 mg/mL and the concentration of the GLP-1 compound is in the range of about 2 to about 10 mg/mL.

Embodiment 58

The pharmaceutical formulation according to embodiment 1-36, wherein the basal insulin is insulin glargine and the insulinotropic GLP-1 compound is ZP10. Embodiment according to embodiment 57, wherein the pH is about 4.

Embodiment 59

The pharmaceutical formulation according to embodiment 58, wherein the zinc content is between 4 an 5 zinc ions per 6 molecules insulin glargine.

EXAMPLES

Example 1

A typical formulation of the fixed combination consisting of the insulin analogue N$^{\epsilon B29}$—(N$^\alpha$—(HOOC(CH$_2$)$_{14}$CO)-γ-Glu) desB30 human insulin and the GLP-1 analogue Arg$^{34}$, Lys$^{26}$(N$^\epsilon$-(γ-Glu(N$^\alpha$-hexadecanoyl)))-GLP-1(7-37), liraglutide, was prepared as follows. Appropriate stock solutions in water were prepared of the insulin analogue and the GLP-1 analogue. The peptide concentrations of both stocks were typically around 10 mM and pH was adjusted to approximately pH 7.7 for the insulin analogue and approximately pH 8.2 for the liraglutide stock solutions. These pH adjustments were done using either NaOH or HClO$_4$ solutions with maximal concentrations of 1.0 N.

The following excipients were mixed from appropriate stock solutions in water in this order: 1) water 2) glycerol (isotonicity modifier) 3) insulin analogue 4) phenol. The addition of phenol before zinc was critical; otherwise a gel was formed. After 15 minutes the zinc acetate was added in three portions: Firstly, a zinc amount corresponding to a concentration of 3 zinc/6 insulin analogue molecules; secondly, a zinc amount corresponding to a concentration of 3 zinc/6 insulin analogue molecules; and thirdly any additional zinc. The solution was equilibrated 5 minutes after each addition. The pH was measured and adjusted to pH 8.2 as described above. This solution was left to equilibrate for approximately 48 hours at 4° C. before an appropriate amount of the liraglutide stock solution was added. Finally, pH was measured and if necessary adjusted to pH 8.2. Following this procedure a formulation was prepared as described in the Table 1.

TABLE 1

| Compound | Stock concentration (mM) | Final concentration (mM) | Volume added (ml) | Order of mixing |
|---|---|---|---|---|
| Insulin analogue | 8.64 | 0.60 | 0.972 | 3 |
| Zinc acetate | 9.54 | 0.80[1)] | 1.174[2)] | 5[2)] |
| Phenol | 500 | 50 | 1.4 | 4 |
| Glycerol | 200 | 16 | 1.12 | 2 |
| Liraglutide | 9.95 | 1.6 | 1.6 | 6[3)] |
| Water | n.a. | n.a. | 7.083 | 1 |

[1)]Corresponding to 8 $Zn^{2+}$/6 insulin analogue molecules
[2)]Was added in three portions: 0.441 ml, 0.440 ml, 0.293 ml, each with 5 minutes in-between and after the last addition
[3)]The solution was equilibrated at 4° C. for approximately 48 hours before the addition of liraglutide Example 2

The protracting mechanism of the insulin analogue $N^{\epsilon B29}$—($N^{\alpha}$—(HOOC(CH$_2$)$_{14}$CO)-γ-Glu) desB30 human insulin has been described to depend on the formation of self-associates in the presence of more than 3 zinc ions per 6 insulin analogue molecules. Hence, if a formulation of insulin analogue $N^{\epsilon B29}$—($N^{\alpha}$—(HOOC(CH$_2$)$_{14}$CO)-γ-Glu) desB30 human insulin contains a significant fraction of the analogue on monomeric form, the formulation is expected to exhibit an undesirable fast-acting component. Furthermore, a high insulin analogue monomer content could compromise the physical stability of the formulation. The presence of the GLP-1 analogue liraglutide in a fixed combination with the insulin analogue $N^{\epsilon B29}$—($N^{\alpha}$—(HOOC(CH$_2$)$_{14}$CO)-γ-Glu) desB30 human insulin may perturb the insulin analogue self-association equilibrium towards the monomeric state with a simultaneously formation of a liraglutide zinc binding complex. It has been demonstrated that liraglutide forms a heptameric self-assembly under formulation relevant conditions, and in the presence of equimolar concentrations of zinc ions, a zinc binding liraglutide diheptamer is formed.

Formulations containing both the insulin analogue $N^{\epsilon B29}$—($N^{\alpha}$—(HOOC(CH$_2$)$_{14}$CO)-γ-Glu) desB30 human insulin and liraglutide were analysed by a size exclusion chromatography (SEC) method with fluorescence detection. The SEC method used a Superose 12 10/300GL column, 50 μl samples were injected and the flow was 0.8 ml/min. Two methods including and excluding phenol were used with the solvent 140 mM NaCl, 10 mM Tris/HCl, pH 7.7, +/−2 mM phenol. Detection was done by one channel with absorption at 276 nm (measuring total peptide amount) and another channel with fluorescence detection (excitation at 310 nm, emission at 380 nm), which was specific for liraglutide.

Under some conditions specific quantification was impossible due to experimental conditions. Here, the amount of insulin analogue on the monomeric form was quantified relative to the total amount of peptide.

Formulations were prepared as described in Example 1. Four formulations each with 0.3 mM and 0.6 mM insulin analogue, respectively, were prepared with zinc contents corresponding to 6, 8, 10, and 12 zinc ions per 6 insulin analogue molecules. These eight formulations were stored at both 4° C. and 37° C.

All formulation contained 0.3 or 0.6 mM insulin analogue, zinc acetate, 1.6 mM liraglutide, 50 mM phenol, 174 mM glycerol, pH 8.2.

The stored formulations were analysed using both the SEC with phenol and the SEC without phenol methods after 0, 2, 4, and 8 weeks of storage. Table 2 and Table 3 show the amounts of insulin analogue on the monomeric form. The shaded areas indicate conditions where an exact quantification was not possible. Therefore, the quantification was also done for insulin analogue monomer relative to total peptide content. This is shown in Table 4 and Table 5.

TABLE 2

| | | % Ins monomer | | | |
|---|---|---|---|---|---|
| | | 0.3 mM Ins | | 0.6 mM Ins | |
| SEC with phenol | | 4° C. | 37° C. | 4° C. | 37° C. |
| 6 Zn/6 ins | 0W | 25.1 | 25.1 | 7.9 | 7.9 |
| | 2W | 59.7 | 55.1 | 19.4 | 17.8 |
| | 4W | | | | |
| 8 Zn/6 ins | 0W | 16.1 | 16.1 | 2.8 | |
| | 2W | 49.0 | 42.6 | 10.3 | |
| | 4W | | | | |
| 10 Zn/6 ins | 0W | 7.9 | 7.9 | 1.5 | |
| | 2W | 36.8 | 32.2 | 2.2 | |
| | 4W | | | | |
| 12 Zn/6 ins | 0W | 6.0 | 6.0 | | |
| | 2W | 24.3 | 23.8 | | |
| | 4W | | | | |

TABLE 3

| | | % Ins monomer | | | |
|---|---|---|---|---|---|
| | | 0.3 mM Ins | | 0.6 mM Ins | |
| SEC without phenol | | 4° C. | 37° C. | 4° C. | 37° C. |
| 6 Zn/6 ins | 0W | 66.4 | 66.4 | 27.9 | 27.9 |
| | 2W | 86.3 | 80.9 | 29.8 | 33.6 |
| | 4W | | | | |
| 8 Zn/6 ins | 0W | 51.9 | 51.9 | 7.0 | |
| | 2W | 72.8 | 68.5 | 16.1 | |
| | 4W | | | | |
| 10 Zn/6 ins | 0W | 28.3 | 28.3 | 2.0 | |
| | 2W | 56.7 | 55.1 | 3.1 | |
| | 4W | | | | |
| 12 Zn/6 ins | 0W | 14.5 | 14.5 | | |
| | 2W | 35.0 | 39.9 | | |
| | 4W | | | | |

TABLE 4

| SEC with phenol | | % Ins monomer of total peptide | | | |
|---|---|---|---|---|---|
| | | 0.3 mM Ins | | 0.6 mM Ins | |
| | | 4° C. | 37° C. | 4° C. | 37° C. |
| 6 Zn/6 Ins | 0 W | 3.8 | 3.8 | 2.0 | 2.0 |
| | 2 W | 8.2 | 7.0 | 4.8 | 4.2 |
| | 4 W | 12.4 | 5.4 | 4.7 | 2.9 |
| | 8 W | 7.8 | 5.5 | 4.5 | 3.4 |
| 8 Zn/6 Ins | 0 W | 2.2 | 2.2 | 0.8 | 0.8 |
| | 2 W | 7.0 | 5.6 | 2.6 | 2.5 |
| | 4 W | 6.8 | 4.2 | 2.3 | 1.8 |
| | 8 W | 6.5 | 4.3 | 2.8 | 1.9 |
| 10 Zn/6 Ins | 0 W | 1.1 | 1.1 | 0.4 | 0.4 |
| | 2 W | 5.2 | 4.3 | 0.6 | 0.8 |
| | 4 W | 4.9 | 2.9 | 0.4 | 0.6 |
| | 8 W | 5.0 | 3.5 | 0.8 | 1.1 |
| 12 Zn/6 Ins | 0 W | 0.9 | 0.9 | 0.8 | 0.8 |
| | 2 W | 3.6 | 3.3 | 0.5 | 0.7 |
| | 4 W | 3.2 | 2.3 | 0.2 | 0.4 |
| | 8 W | 4.2 | 2.9 | 0.4 | 0.5 |

TABLE 5

| SEC without phenol | | % Ins monomer of total peptide | | | |
|---|---|---|---|---|---|
| | | 0.3 mM Ins | | 0.6 mM Ins | |
| | | 4° C. | 37° C. | 4° C. | 37° C. |
| 6 Zn/6 Ins | 0 W | 16.3 | 16.3 | 7.5 | 7.5 |
| | 2 W | 16.6 | 12.1 | 8.3 | 8.8 |
| | 4 W | 10.1 | 8.8 | 6.3 | 5.5 |
| | 8 W | 13.1 | 10.8 | 9.1 | 8.1 |
| 8 Zn/6 Ins | 0 W | 8.4 | 8.4 | 2.0 | 2.0 |
| | 2 W | 11.3 | 10.1 | 4.3 | 5.0 |
| | 4 W | 8.3 | 7.4 | 2.9 | 3.0 |
| | 8 W | 11.1 | 9.1 | 4.9 | 4.9 |
| 10 Zn/6 Ins | 0 W | 4.5 | 4.5 | 0.5 | 0.5 |
| | 2 W | 8.5 | 8.3 | 0.8 | 1.3 |
| | 4 W | 6.3 | 5.6 | 0.4 | 0.8 |
| | 8 W | 8.7 | 7.3 | 1.3 | 2.4 |
| 12 Zn/6 Ins | 0 W | 2.3 | 2.3 | 0.7 | 0.7 |
| | 2 W | 5.6 | 6.1 | 0.8 | 1.1 |
| | 4 W | 4.3 | 4.1 | 0.2 | 0.5 |
| | 8 W | 6.9 | 7.0 | 0.6 | 1.4 |

The amount of zinc binding liraglutide di-heptamer was readily measured using the fluorescence detection. Table 6 and Table 7 show the measured amounts in the analysed samples.

TABLE 6

| SEC with phenol | | % Diheptamer of total Liraglutide | | | |
|---|---|---|---|---|---|
| | | 0.3 mM Ins | | 0.6 mM Ins | |
| | | 4° C. | 37° C. | 4° C. | 37° C. |
| 6 Zn/6 Ins | 0 W | 0 | 0 | 0 | 0 |
| | 2 W | 0 | 0 | 0 | 0 |
| | 4 W | 0 | 0 | 0 | 0 |
| | 8 W | 0 | 0 | 0 | 0 |
| 8 Zn/6 Ins | 0 W | 0 | 0 | 0 | 0 |
| | 2 W | 0 | 0 | 0 | 0.3 |
| | 4 W | 0 | 0 | 0 | 0.4 |
| | 8 W | 0 | 0 | 0 | 0.4 |
| 10 Zn/6 Ins | 0 W | 0 | 0 | 0 | 0 |
| | 2 W | 0 | 0 | 0 | 1.2 |
| | 4 W | 0 | 0 | 0 | 1.5 |
| | 8 W | 0 | 0 | 0.1 | 2.1 |
| 12 Zn/6 Ins | 0 W | 0 | 0 | 0.4 | 0.4 |
| | 2 W | 0 | 0 | 0.6 | 15.4 |
| | 4 W | 0 | 0 | 0.4 | 15.2 |
| | 8 W | 0 | 0.1 | 0.8 | 15.6 |

TABLE 7

| SEC without phenol | | % Liraglutide diheptamer | | | |
|---|---|---|---|---|---|
| | | 0.3 mM Ins | | 0.6 mM Ins | |
| | | 4° C. | 37° C. | 4° C. | 37° C. |
| 6 Zn/6 Ins | 0 W | 0 | 0 | 0 | 0 |
| | 2 W | 0 | 0 | 0 | 0 |
| | 4 W | 0 | 0 | 0 | 0 |
| | 8 W | 0 | 0 | 0 | 0.1 |
| 8 Zn/6 Ins | 0 W | 0 | 0 | 0 | 0 |
| | 2 W | 0 | 0 | 0 | 0.3 |
| | 4 W | 0 | 0 | 0 | 0.2 |
| | 8 W | 0 | 0 | 0 | 0.4 |
| 10 Zn/6 Ins | 0 W | 0 | 0 | 0 | 0.1 |
| | 2 W | 0 | 0 | 0 | 1.3 |
| | 4 W | 0 | 0 | 0 | 1.1 |
| | 8 W | 0 | 0 | 0 | 2.4 |
| 12 Zn/6 Ins | 0 W | 0 | 0 | 0.3 | 0.3 |
| | 2 W | 0 | 0 | 0.5 | 16.7 |
| | 4 W | 0 | 0 | 0.3 | 13.5 |
| | 8 W | 0 | 0.1 | 0.8 | 17.7 |

Example 3

Following the procedure in Example 1 four formulations were prepared with the compositions shown in Table 8. In Formulation 3 the glycylglycine buffer was added together with the water. In Formulation 4 the phosphate buffer was added after the zinc acetate was added. This was done in order to minimise zinc-phosphate precipitation. The used insulin analogue was $N^{\epsilon B29}$—($N^{\alpha}$—(HOOC(CH$_2$)$_{14}$CO)-γ-Glu) desB30 human insulin.

The physical stability of the four pharmaceutical compositions was evaluated by means of an accelerated stressed test. The stressed test was performed as a rotation test. 50 μL air was added to each of 5 cartridges (glass vials) of each formulation. The cartridges were rotated with a frequency of 30 rotations per minute for 4 hours daily. The inspection of the cartridges was followed daily or as required. The turbidity of the formulation was characterized by nephelometric measurement and specified in "Nephelometric Turbidity Unit" (NTU). Physical instability of the protein was characterised by high turbidity measurements.

This rotation test is shown in FIG. 1. It revealed that the formulation with the insulin analogue and liraglutide combined and formulated at pH 7.7 (Formulation 3) was less stable than the insulin analogue formulated alone at pH 7.4 (Formulation 1) and probably had an unacceptable stability for further development. Formulation 4 also contained the insulin analogue and liraglutide combination but was formulated at pH 8.2. This formulation had an only marginally lower physical stability than the insulin analogue alone. Hence, this comparison illustrated that combining the insulin analogue and liraglutide without any optimisation resulted in an unstable formulation. Increasing the pH to pH 8.2, however, resulted in much improved physical stability comparable to that of insulin analogue alone.

TABLE 8

| | Formulation 1 | Formulation 2 | Formulation 3 | Formulation 4 |
|---|---|---|---|---|
| Insulin analogue (mM) | 0.6 | n.a. | 0.6 | 0.6 |
| Zinc acetate (mM) | 0.6 | n.a. | 0.6 | 0.6 |
| Liraglutide (mM) | n.a. | 1.6 | 1.6 | 1.6 |
| Phenol (mM) | 16 | 58 | 40 | 40 |
| m-cresol (mM) | 16 | n.a. | n.a. | n.a. |
| Glycerol (mM) | 174 | 174 | 174 | 174 |
| NaCl (mM) | 10 | n.a. | 10 | 10 |
| Phosphate (mM) | n.a. | 8 | n.a. | 8 |
| Glycylglycine (mM) | n.a. | n.a. | 8 | n.a. |
| pH | 7.4 | 7.7 | 7.7 | 8.2 |

Example 4

In another rotation test performed as described in Example 3, four combination formulations containing both the insulin analogue $N^{\epsilon B29}$—($N^\alpha$—(HOOC(CH$_2$)$_{14}$CO)-γ-Glu) desB30 human insulin and liraglutide and two references with the insulin analogue and liraglutide alone were tested.

The formulations were prepared as described in Example 1 and their compositions are shown in Table 9.

TABLE 9

| | Form. 1 | Form. 2 | Form. 3 | Form. 4 | Form. 5 | Form. 6 |
|---|---|---|---|---|---|---|
| Insulin analogue (mM) | 0.6 | n.a. | 0.6 | 0.6 | 0.6 | 0.3 |
| Zinc acetate (mM) | 0.6 (= 6 Zn$^{2+}$/6 ins) | n.a. | 0.8 (= 8 Zn$^{2+}$/6 ins) | 1.0 (= 10 Zn$^{2+}$/6 ins) | 1.2 (= 12 Zn$^{2+}$/6 ins) | 0.5 (= 10 Zn$^{2+}$/6 ins) |
| Liraglutide (mM) | n.a. | 1.6 | 1.6 | 1.6 | 1.6 | 1.6 |
| Phenol (mM) | 16 | 58 | 50 | 50 | 50 | 50 |
| m-cresol (mM) | 16 | n.a. | n.a. | n.a. | n.a. | n.a. |
| Glycerol (mM) | 174 | 174 | 174 | 174 | 174 | 174 |
| NaCl (mM) | 10 | n.a. | n.a. | n.a. | n.a. | n.a. |
| Phosphate (mM) | n.a. | 8 | n.a. | n.a. | n.a. | n.a. |
| pH | 7.4 | 8.2 | 8.2 | 8.2 | 8.2 | 8.2 |

Figure 2:
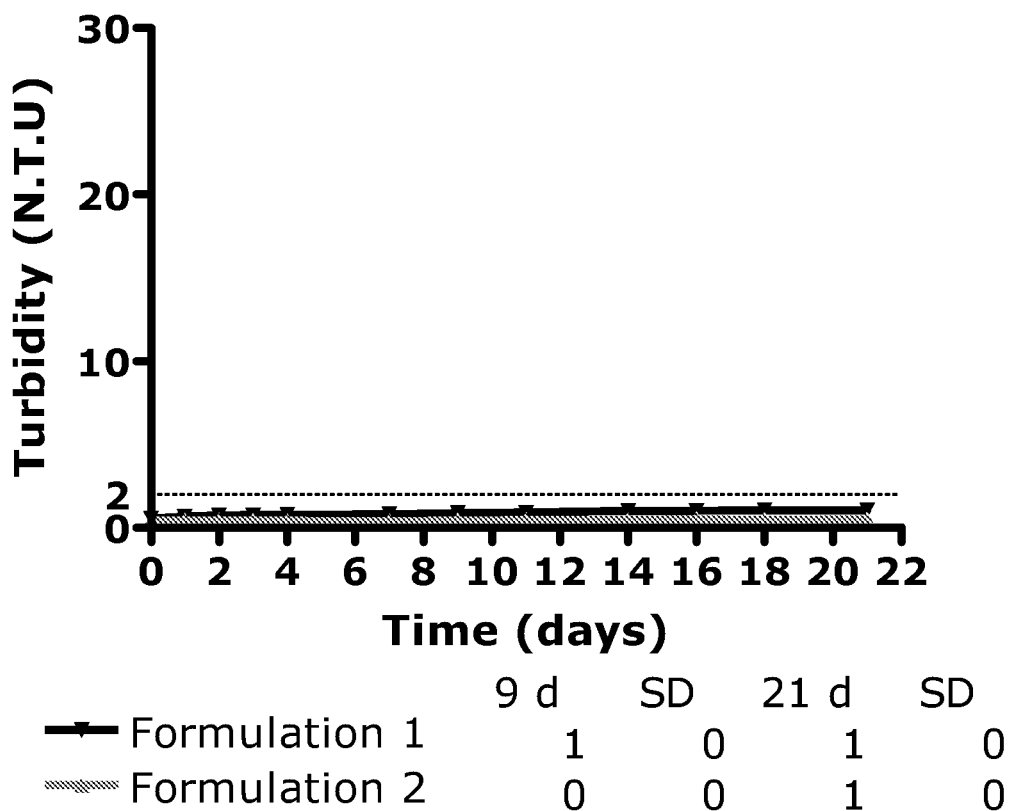
FIG. 2-4 show the results from a rotation test
Figure 3:
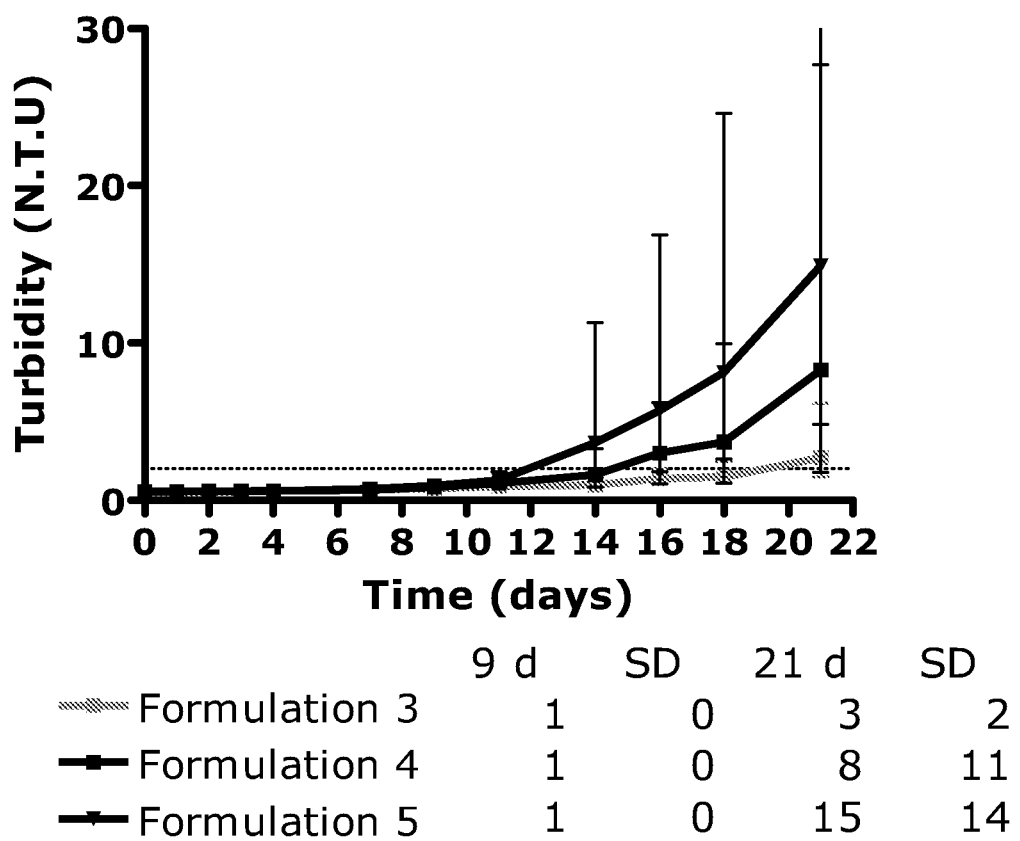
Figure 4:
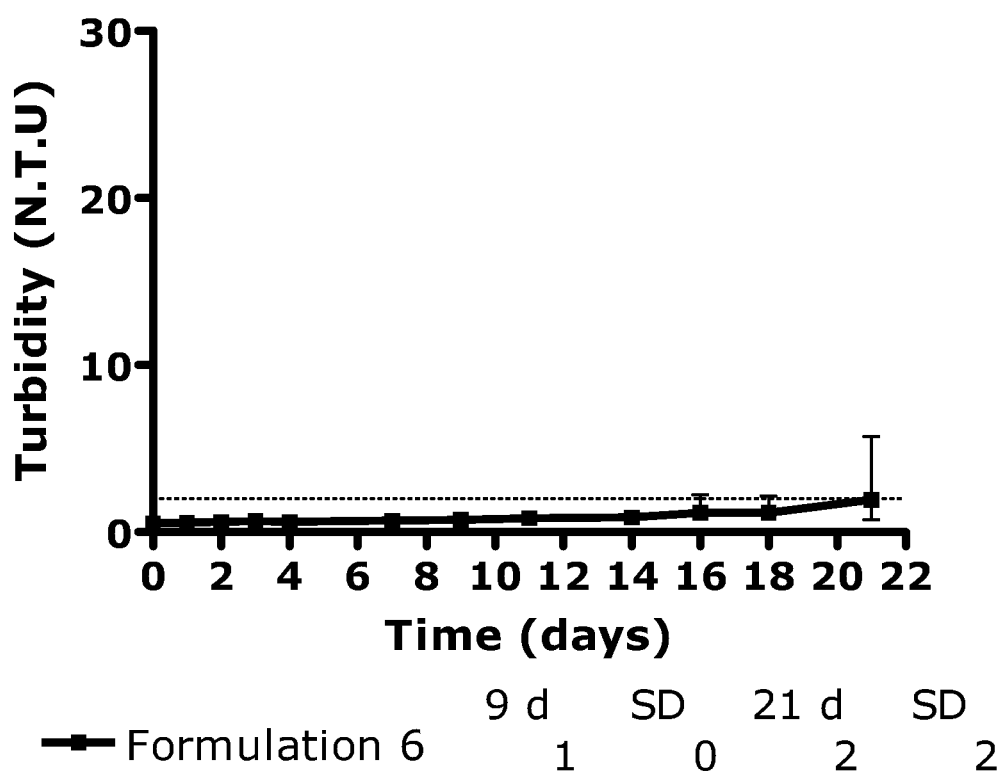

The results from the rotation test are shown in FIG. 2-4.

Formulation 3 contained 8 zinc/6 insulin analogue molecules and had a comparable stability to the both references with the insulin analogue (with 6 zinc/6 insulin analogue molecules) and liraglutide alone. Formulation 6 only contained 0.3 mM insulin analogue but required 10 zinc/6 insulin analogue molecules in order to exhibit a similar stability as the reference. This indicated that higher zinc content relative to the amount of insulin analogue was required in order to achieve the same stability as the insulin analogue reference alone with 6 zinc ions/6 insulin analogue molecules.

Example 5

Figure 5:
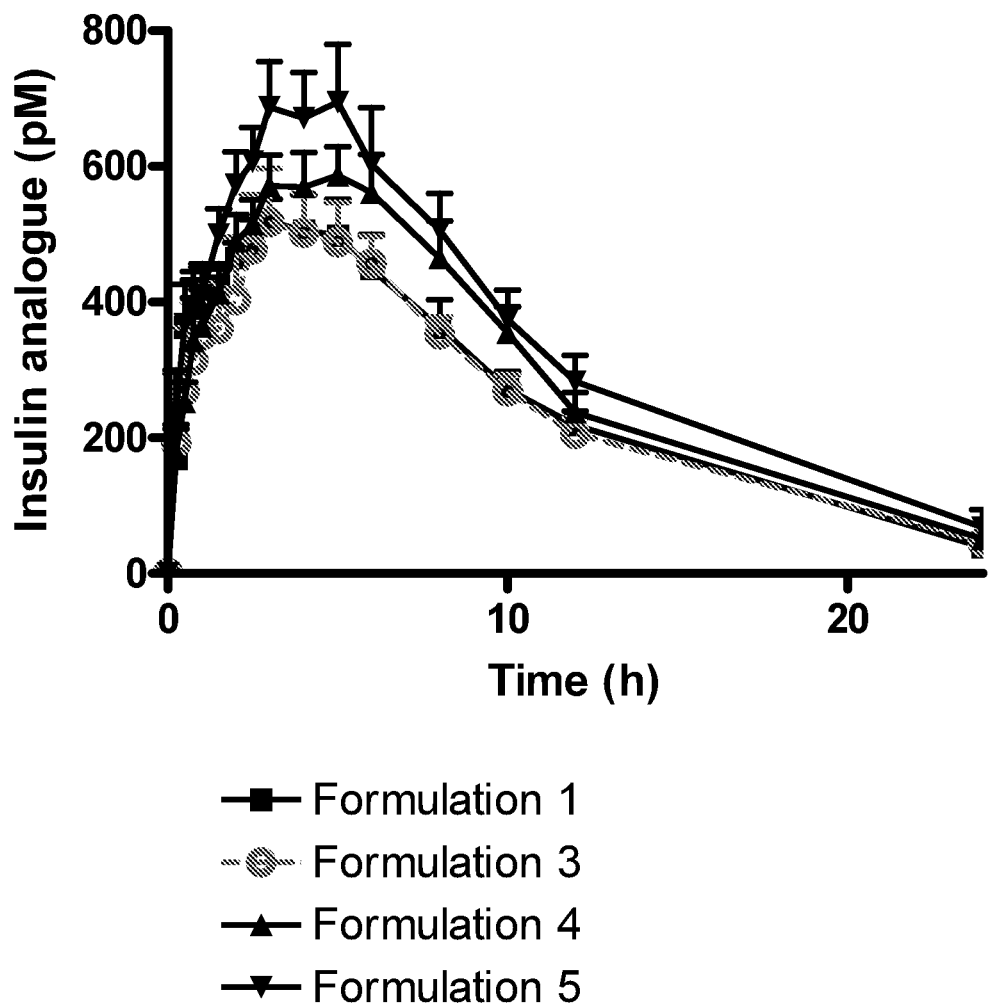
FIG. 5-8 show the pharmacokinetic (PK) properties of fixed combination formulations with the insulin analogue $N^{\epsilon B29}$—($N^{\alpha}$—(HOOC(CH$_2$)$_{14}$CO)-γ-Glu) desB30 human insulin and liraglutide examined in pigs.
Figure 6:
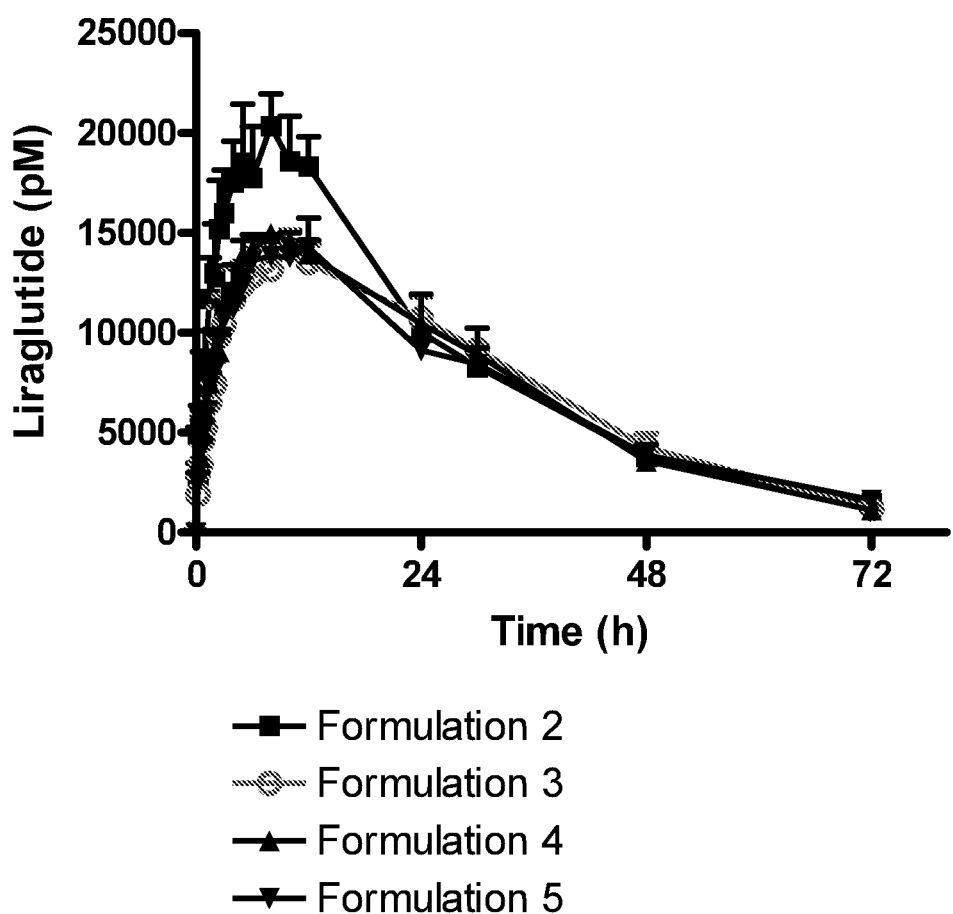

The pharmacokinetic (PK) properties of fixed combination formulations with the insulin analogue $N^{\epsilon B29}$—($N^\alpha$—(HOOC(CH$_2$)$_{14}$CO)-γ-Glu) desB30 human insulin and liraglutide were examined in pigs. The appearances of the two peptides in the blood stream were measured by standard assay techniques for up to 72 hours after injection. For clarity, however, only the first 24 hours are shown for the insulin analogue. The results are shown in FIG. 5 and FIG. 6 as means of the six replica and shown with standard error of the mean. Three combination formulations and two references were prepared as outlined in Example 1. Their compositions are shown in Table 10. The PK appearance curve for the insulin analogue is shown in FIG. 5 and the PK appearance curve for liraglutide is shown in FIG. 6.

TABLE 10

| | Form. 1 | Form. 2 | Form. 3 | Form. 4 | Form. 5 |
|---|---|---|---|---|---|
| Insulin analogue (mM) | 0.6 | n.a. | 0.6 | 0.6 | 0.6 |
| Zinc acetate (mM) | 0.6 (= 6 Zn$^{2+}$/6 ins) | n.a. | 0.8 (= 8 Zn$^{2+}$/6 ins) | 1.0 (= 10 Zn$^{2+}$/6 ins) | 1.2 (= 12 Zn$^{2+}$/6 ins) |
| Liraglutide (mM) | n.a. | 1.6 | 1.6 | 1.6 | 1.6 |
| Phenol (mM) | 50 | 50 | 50 | 50 | 50 |
| Glycerol (mM) | 174 | 174 | 174 | 174 | 174 |
| pH | 8.2 | 8.2 | 8.2 | 8.2 | 8.2 |

The appearance of the insulin analogue in the combination is critically for several reasons: A fast-acting component will give rise to an unexpected early on-set of effect. An increased bioavailability will also result in a larger blood glucose lowering effect and subsequently an adjustment of the dose would be required. It is interesting to conclude that the combination formulation 3 (formulated with 8 zinc/6 insulin analogue molecules) exhibited a very similar insulin appearance curve compared to the curve for the insulin analogue alone (Formulation 1). Hence, a combination formulation with 8 zinc/6 insulin analogue molecules exhibited very similar insulin PK properties when compared to the insulin analogue alone. All combination formulations exhibited very similar liraglutide appearance curves (Formulations 3-5).

Example 6

The pharmacokinetic (PK) properties of other fixed combination formulations with the insulin analogue $N^{\epsilon B29}$—($N^\alpha$—(HOOC(CH$_2$)$_{14}$CO)-γ-Glu) desB30 human insulin and liraglutide in a different ratio were likewise examined in pigs. This ratio enables a larger amount of the insulin analogue relative to liraglutide to be delivered to the patient in a single injection. An equal dose of insulin was administered to the pigs of both the insulin analogue reference (Formulation 1) and the combinations (Formulations 3-5). The appearances of the two peptides in the blood stream were measured by standard assay techniques for up to 72 hours after injection.

Figure 7:
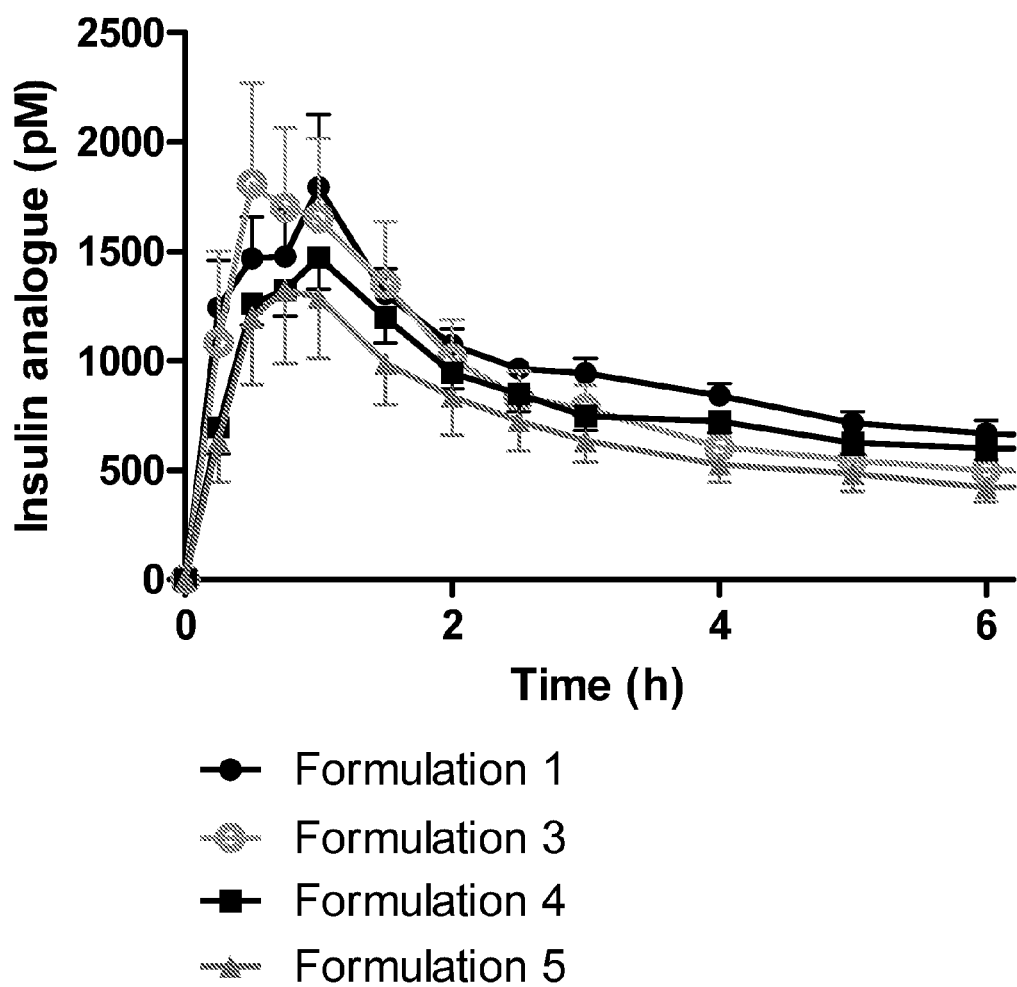
Figure 8:
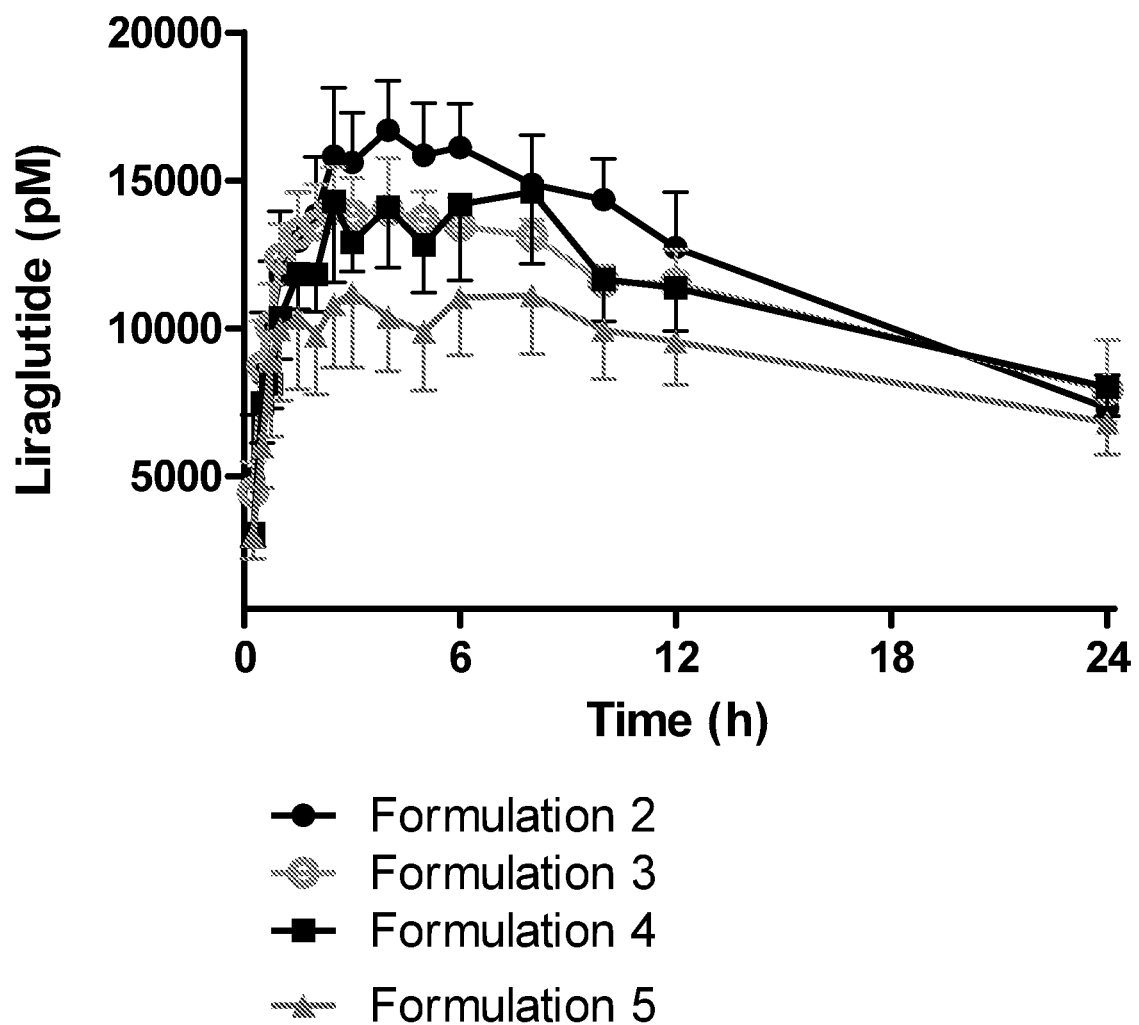

For clarity, however, only the first 6 hours and 24 hours, respectively, are shown. The results are shown in FIG. 7 and FIG. 8 as means of the six replica and shown with standard error of the mean. Three combination formulations and two references were prepared as outlined in Example 1. Their compositions are shown in Table 11. The PK appearance curve for the insulin analogue is shown in FIG. 7 and the PK appearance curve for liraglutide is shown in FIG. 8.

TABLE 11

|  | Form. 1 | Form. 2 | Form. 3 | Form. 4 | Form. 5 |
|---|---|---|---|---|---|
| Insulin analogue (mM) | 0.6 | n.a. | 1.2 | 1.2 | 1.2 |
| Zinc acetate (mM) | 0.6 | n.a. | 1.2 | 1.4 | 1.6 |
|  | (= 6 $Zn^{2+}$/6 ins) |  | (= 6 $Zn^{2+}$/6 ins) | (= 7 $Zn^{2+}$/6 ins) | (= 8 $Zn^{2+}$/6 ins) |
| Liraglutide (mM) | n.a. | 1.6 | 1.6 | 1.6 | 1.6 |
| Phenol (mM) | 50 | 50 | 50 | 50 | 50 |
| Glycerol (mM) | 214 | 214 | 214 | 214 | 214 |
| pH | 8.2 | 8.2 | 8.2 | 8.2 | 8.2 |

Compared to the insulin analogue reference (Formulation 1) the combination with 6 $Zn^{2+}$/6 insulin molecules (Formulation 3) exhibited a minor shoulder with an earlier on-set than the main peak of the reference. Increasing the zinc content to 7 $Zn^{2+}$/6 insulin molecules (Formulation 4) resulted in an insulin analogue appearance curve much more similar to that of the insulin reference (Formulation 1). Increasing the zinc content further to 8 $Zn^{2+}$/6 insulin molecules (Formulation 5) did not result in any further improvement. No statistically significant differences were found between the PK appearance curves for liraglutide in the three combinations (Formulations 3-5) and liraglutide alone (Formulation 2). This indicated that a zinc content of 7 $Zn^{2+}$/6 insulin molecules for the 1.2 mM insulin analogue-1.6 mM liraglutide combination was preferable in order to obtain a similar PK appearance curve for the insulin analogue in the combination compared to the analogue alone.

Example 7

The influence of pH on the content of insulin analogue $N^{\epsilon B29}$—($N^{\alpha}$—(HOOC(CH$_2$)$_{14}$CO)-γ-Glu) desB30 human insulin monomer in combinations with liraglutide was investigated. Three formulations were prepared as outlined in Example 1 but adjusted to pH 8.2, pH 7.7, and pH 7.4. The composition of all three formulations was: 0.6 mM insulin analogue, 0.8 mM zinc acetate (8 zinc per 6 insulin analogue molecules), 1.6 mM liraglutide, 50 mM phenol, 214 mM glycerol. After preparation the formulations were stored at 4° C. for some weeks before the first measurement at time point 0 weeks. Hereafter the formulations were stored at both 5° C. and 37° C. and analysed after further 2 and 4 weeks of storage at the two temperatures. The formulations were analysed using the SEC method described in Example 2. Both versions with and without phenol were used.

The relative contents of insulin analogue monomer compared to total insulin analogue measured by the SEC analysis with phenol and without phenol are shown in Table 12 and Table 13, respectively. In both SEC methods and at both temperatures, decreasing pH resulted in lower insulin analogue monomer content at each time point of measurement. This indicated that pH is an important factor for controlling and modulating the insulin monomer content in the combinations with liraglutide. A lower insulin monomer content could be obtained by using a pH lower than pH 8.2, e.g. pH 7.7.

TABLE 12

|  | % Monomer Ins | | |
|---|---|---|---|
| SEC with phenol | 0 W | 2 W | 4 W |
| pH 8.2 (4° C.) | 12.4 | 8.1 | 8.8 |
| pH 7.7 (4° C.) | 2.5 | 2.8 | 2.8 |
| pH 7.4 (4° C.) | 1.1 | 1.2 | 1.1 |
| pH 8.2 (37° C.) | 12.4 | 8.2 | 7.8 |
| pH 7.7 (37° C.) | 2.5 | 3.1 | 2.3 |
| pH 7.4 (37° C.) | 1.1 | 1.5 | 1.1 |

TABLE 13

|  | % Monomer Ins | | |
|---|---|---|---|
| SEC without phenol | 0 W | 2 W | 4 W |
| pH 8.2 (4° C.) | 12.5 | 13.7 | 13.6 |
| pH 7.7 (4° C.) | 1.7 | 3.5 | 4.3 |
| pH 7.4 (4° C.) | 0.7 | 1.3 | 1.6 |
| pH 8.2 (37° C.) | 12.5 | 15.2 | 17.6 |
| pH 7.7 (37° C.) | 1.7 | 4.1 | 4.6 |
| pH 7.4 (37° C.) | 0.7 | 1.9 | 2.0 |

The liraglutide diheptamer contents were also measured in a similar fashion and these results are shown in Table 14 and Table 15 for the SEC method with phenol and without phenol, respectively.

TABLE 14

|  | % Liraglutide diheptamer | | |
|---|---|---|---|
| SEC with phenol | 0 W | 2 W | 4 W |
| pH 8.2 (4° C.) | 0.0 | 0.1 | 0.1 |
| pH 7.7 (4° C.) | 0.1 | 0.1 | 0.1 |
| pH 7.4 (4° C.) | 0.8 | 0.4 | 0.4 |
| pH 8.2 (37° C.) | 0.0 | 0.4 | 0.6 |
| pH 7.7 (37° C.) | 0.1 | 4.6 | 6.1 |
| pH 7.4 (37° C.) | 0.8 | 18.0 | 21.6 |

TABLE 15

|  | % Liraglutide diheptamer | | |
|---|---|---|---|
| SEC without phenol | 0 W | 2 W | 4 W |
| pH 8.2 (4° C.) | 0.0 | 0.0 | 0.0 |
| pH 7.7 (4° C.) | 0.1 | 0.1 | 0.1 |
| pH 7.4 (4° C.) | 0.9 | 0.4 | 0.3 |
| pH 8.2 (37° C.) | 0.0 | 0.3 | 0.5 |
| pH 7.7 (37° C.) | 0.1 | 4.4 | 5.2 |
| pH 7.4 (37° C.) | 0.9 | 16.6 | 19.0 |

Example 8

The study described in Example 7 also contained an insulin analogue $N^{\epsilon B29}$—($N^{\alpha}$—(HOOC(CH$_2$)$_{14}$CO)-γ-Glu) desB30 human insulin-liraglutide combination formulation containing a low concentration of histidine. The amino acid was intended to act as a zinc buffer in the presence of an increased zinc content. Formulation 1 was composed of 0.6 mM insulin analogue, 0.8 mM zinc acetate (8 zinc per 6 insulin analogue molecules), 1.6 mM liraglutide, 50 mM phenol, 214 mM glycerol, with pH adjusted to pH 8.2. Formulation 2 was composed of 0.6 mM insulin analogue, 1.0 mM zinc acetate (10 zinc per 6 insulin analogue molecules), 1.6 mM liraglutide, 50 mM phenol, 214 mM glycerol, 0.5 mM histidine, pH adjusted to pH 8.2. Both formulations were basically produced as outlined in Example 1, the histidine was added as the final excipient after liraglutide. The formulations were analysed as described in Example 2 and Example 7.

The relative contents of insulin analogue monomer compared to total insulin analogue measured by the SEC analysis with phenol and without phenol are shown in Table 16 and Table 17, respectively. Formulation 2 with 10 zinc/6 insulin molecules and 0.5 mM histidine present contained less insulin monomer over time at both temperatures than Formulation 1 with only 8 zinc/6 insulin molecules.

TABLE 16

| SEC with phenol | % Ins monomer | | |
|---|---|---|---|
| | 0 W | 2 W | 4 W |
| Formulation 1 (4° C.) | 12.4 | 8.1 | 8.8 |
| Formulation 2 (4° C.) | 3.2 | 3.0 | 3.1 |
| Formulation 1 (37° C.) | 12.4 | 8.2 | 7.8 |
| Formulation 2 (37° C.) | 3.2 | 3.7 | 3.4 |

TABLE 17

| SEC without phenol | % Ins monomer | | |
|---|---|---|---|
| | 0 W | 2 W | 4 W |
| Formulation 1 (4° C.) | 12.5 | 13.7 | 13.6 |
| Formulation 2 (4° C.) | 2.4 | 4.0 | 4.5 |
| Formulation 1 (37° C.) | 12.5 | 15.2 | 17.6 |
| Formulation 2 (37° C.) | 2.4 | 5.1 | 6.3 |

The liraglutide diheptamer contents were also measured in a similar fashion and these results are shown in Table 18 and Table 19 for the SEC method with phenol and without phenol, respectively.

TABLE 18

| SEC with phenol | % Liraglutide diheptamer | | |
|---|---|---|---|
| | 0 W | 2 W | 4 W |
| Formulation 1 (4° C.) | 0.0 | 0.1 | 0.1 |
| Formulation 2 (4° C.) | 0.1 | 0.2 | 0.2 |
| Formulation 1 (37° C.) | 0.0 | 0.4 | 0.6 |
| Formulation 2 (37° C.) | 0.1 | 1.9 | 3.6 |

TABLE 19

| SEC without phenol | % Liraglutide diheptamer | | |
|---|---|---|---|
| | 0 W | 2 W | 4 W |
| Formulation 1 (4° C.) | 0.0 | 0.0 | 0.0 |
| Formulation 2 (4° C.) | 0.1 | 0.1 | 0.1 |
| Formulation 1 (37° C.) | 0.0 | 0.3 | 0.5 |
| Formulation 2 (37° C.) | 0.1 | 1.8 | 3.0 |

Example 9

The study described in Example 7 also contained an insulin analogue $N^{\epsilon B29}$—($N^{\alpha}$—(HOOC(CH$_2$)$_{14}$CO)-γ-Glu) desB30 human insulin-liraglutide combination composed of 0.3 mM insulin analogue, 0.8 mM zinc acetate (16 zinc per 6 insulin analogue molecules), 1.6 mM liraglutide, 50 mM phenol, 214 mM glycerol, adjusted to pH 8.2.

The relative contents of insulin analogue monomer compared to total insulin analogue measured by the SEC analysis with phenol and without phenol (as described in Example 2) are shown in Table 20 and Table 21, respectively.

TABLE 20

| SEC with phenol | % Monomer insulin | | |
|---|---|---|---|
| | 0 W | 2 W | 4 W |
| 4° C. | 7.9 | 7.0 | 6.8 |
| 37° C. | 7.9 | 6.2 | 5.9 |

TABLE 21

| SEC without phenol | % Monomer insulin | | |
|---|---|---|---|
| | 0 W | 2 W | 4 W |
| 4° C. | 7.1 | 8.3 | 8.6 |
| 37° C. | 7.1 | 8.6 | 10.0 |

The liraglutide diheptamer contents were also measured in a similar fashion and these results are shown in Table 22 and Table 23 for the SEC method with phenol and without phenol, respectively.

TABLE 22

| SEC with phenol | % Liraglutide diheptamer | | |
|---|---|---|---|
| | 0 W | 2 W | 4 W |
| 4° C. | 0.1 | 0.1 | 0.1 |
| 37° C. | 0.1 | 1.8 | 2.7 |

TABLE 23

| SEC without phenol | % Liraglutide diheptamer | | |
|---|---|---|---|
| | 0 W | 2 W | 4 W |
| 4° C. | 0.1 | 0.1 | 0.1 |
| 37° C. | 0.1 | 1.9 | 2.5 |

Example 10

Formulations combining insulin glargine and the exendin-4 analogue ZP10 (also known as AVE0010) were prepared. The ZP10 exendin-4 analogue is described in Thorkildsen et al. (2003), JPET 307:490-496 and has the systematic name [des-Pro38]exendin-4-(1-39)yl-Lys-Lys-Lys-Lys-Lys-Lys-NH2. From appropriate stock solutions the following compositions were prepared by dilution in water: Formulation 1 consisted of 0.6 mM insulin glargine, 0.46 mM zinc acetate (4.6 zinc/6 insulin glargine), 60 µM ZP10. Formulation 2 consisted of 0.6 mM insulin glargine, 0.6 mM zinc acetate (6 zinc/6 insulin glargine), 60 µM ZP10. Both formulations were adjusted to about pH 4.0 using HCl and NaOH and stored at ambient temperature for three days. After storage both formulations were still about pH 4.0. The two formulations maintained clear solutions immediately after preparation and after the storage at ambient temperature.

The invention claimed is:

1. A soluble pharmaceutical composition for parenteral administration, which comprises an insulinotropic GLP-1 compound, a basal insulin peptide, pharmaceutically acceptable additives and zinc,
   wherein the insulinotropic GLP-1 compound is $Arg^{34}$, $Lys^{26}(N^{\epsilon}\text{-}(\gamma\text{-}Glu(N^{\alpha}\text{-}hexadecanoyl)))\text{-}GLP\text{-}1(7\text{-}37)$,
   wherein the basal insulin is $N^{\epsilon B29}\text{-}(N^{\alpha}\text{-}(HOOC(CH_2)_{14}CO)\text{-}\gamma\text{-}Glu)$ desB30 human insulin,
   wherein the zinc content is between 7 and 12 Zn ions per 6 insulin molecules, and
   wherein the pH is between 7.7 and 8.2.

2. A pharmaceutical composition according to claim 1, wherein the concentration of the basal insulin is in the range from about 1.5 to about 8 mg/mL and the concentration of the GLP-1 compound is in the range of about 2 to about 10 mg/mL.

3. A pharmaceutical composition according to claim 1, further comprising histidine.

* * * * *

UNITED STATES PATENT AND TRADEMARK OFFICE
CERTIFICATE OF CORRECTION

| | | |
|---|---|---|
| PATENT NO. | : 8,937,042 B2 | Page 1 of 1 |
| APPLICATION NO. | : 12/741923 | |
| DATED | : January 20, 2015 | |
| INVENTOR(S) | : Plum et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Twenty-ninth Day of December, 2015

Michelle K. Lee
*Director of the United States Patent and Trademark Office*